United States Patent
Salameh et al.

(10) Patent No.: US 7,101,378 B2
(45) Date of Patent: Sep. 5, 2006

(54) SURGICAL TREATMENT DEVICE

(75) Inventors: Fadi Salameh, Tokyo (JP); Takaaki Komiya, Hachioji (JP); Ichiro Takahashi, Sagamihara (JP); Tateyumi Nakagawa, Fuchu (JP)

(73) Assignee: Olympus Corporation, Tokyo (JP)

( * ) Notice: Subject to any disclaimer, the term of this patent is extended or adjusted under 35 U.S.C. 154(b) by 309 days.

(21) Appl. No.: 10/331,745

(22) Filed: Dec. 30, 2002

(65) Prior Publication Data

US 2004/0092953 A1 May 13, 2004

(30) Foreign Application Priority Data

Aug. 20, 2002 (JP) .............................. 2002-239615

(51) Int. Cl.
*A61B 17/24* (2006.01)
*A61B 10/00* (2006.01)

(52) U.S. Cl. ...................................... 606/113; 600/564
(58) Field of Classification Search ................ 606/159, 606/200, 113, 170–171, 167, 127; 600/564–567, 600/581–583
See application file for complete search history.

(56) References Cited

U.S. PATENT DOCUMENTS

| 5,224,488 A | * | 7/1993 | Neuffer ........................ 600/564 |
| 5,554,163 A | * | 9/1996 | Shturman ..................... 606/159 |
| 6,287,304 B1 | * | 9/2001 | Eggers et al. .................. 606/37 |
| 6,331,166 B1 | * | 12/2001 | Burbank et al. ............. 600/567 |
| 6,440,147 B1 | | 8/2002 | Lee et al. |

FOREIGN PATENT DOCUMENTS

JP    55-116345    9/1980

* cited by examiner

*Primary Examiner*—(Jackie) Tan-Uyen T. Ho
(74) *Attorney, Agent, or Firm*—Scully, Scott, Murphy & Presser, P.C.

(57) ABSTRACT

A biotissue excising instrument includes a tubular sheath inserted into a body, manipulator inserted into the sheath through leading end of the manipulator and having a loop portion that can be unfolded and contracted to accommodate biotissue to be excised. A slit is formed leading end the sheath to project and sink loop portion of the treatment portion so that manipulator is advanced or retreated to laterally project or sink the loop portion out of or into the or contract the loop portion, the sheath, and a treatment portion provided at thus excising the biotissue loop portion.

21 Claims, 19 Drawing Sheets

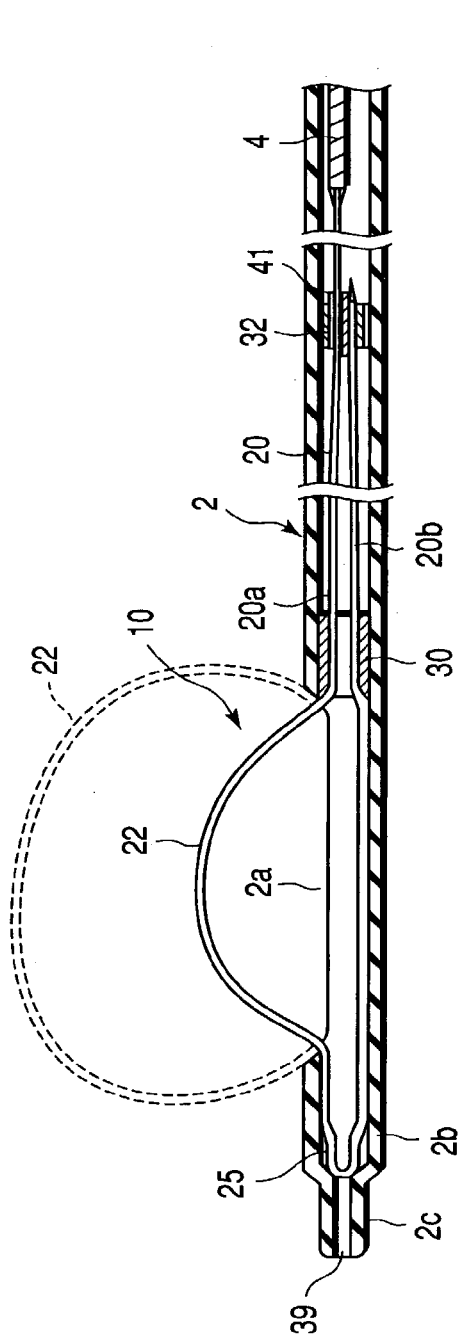
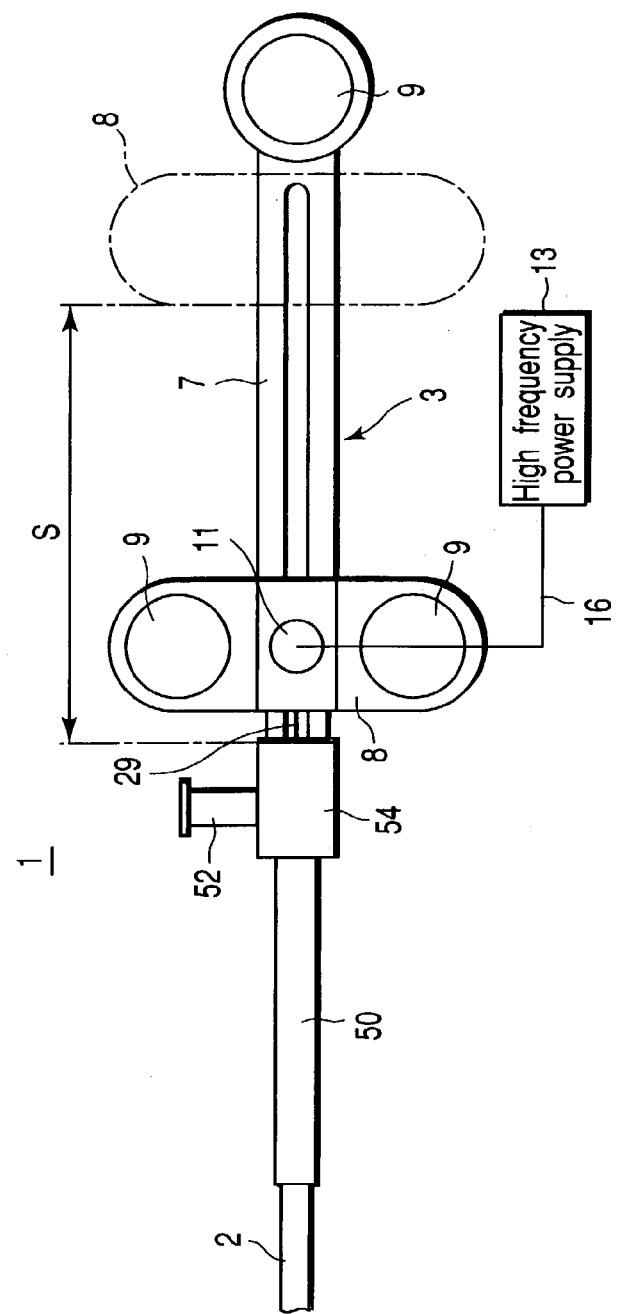
F I G. 1A
F I G. 1B

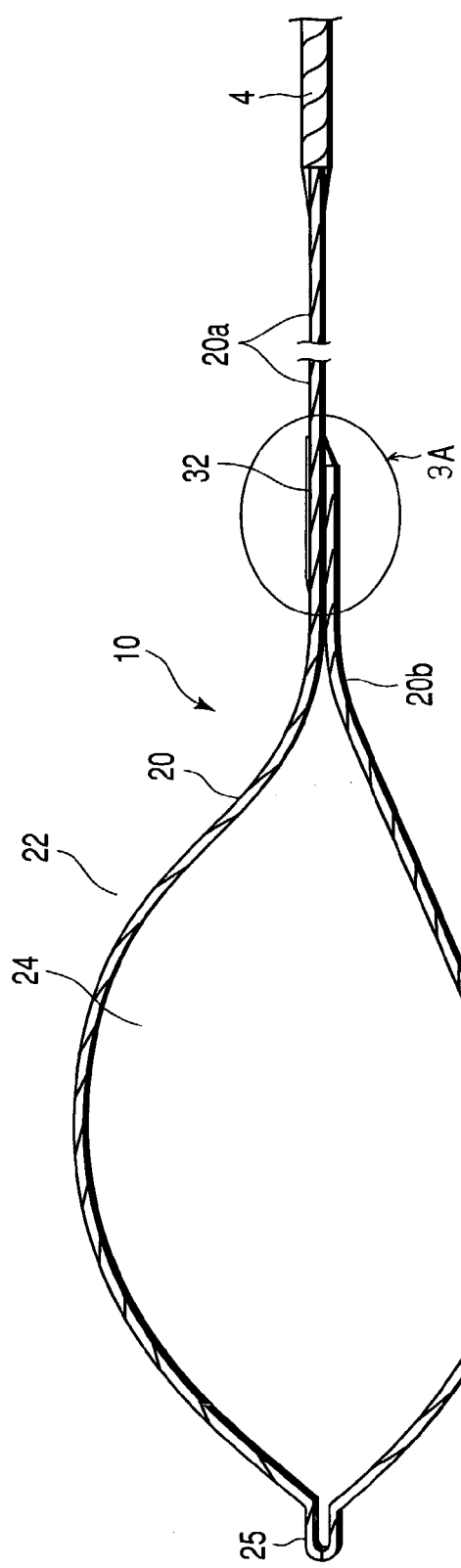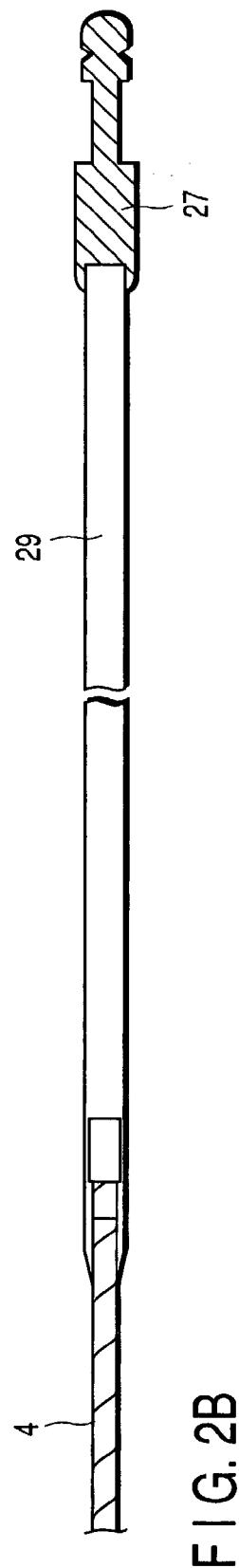
FIG. 2A
FIG. 2B

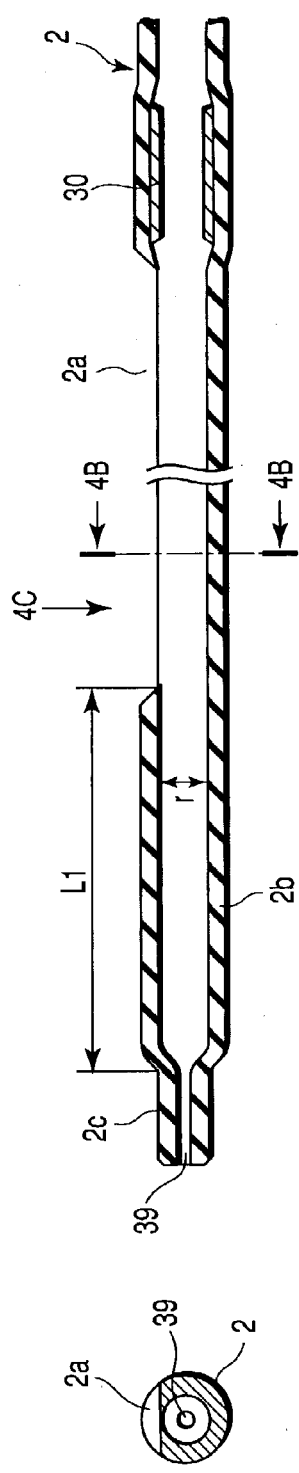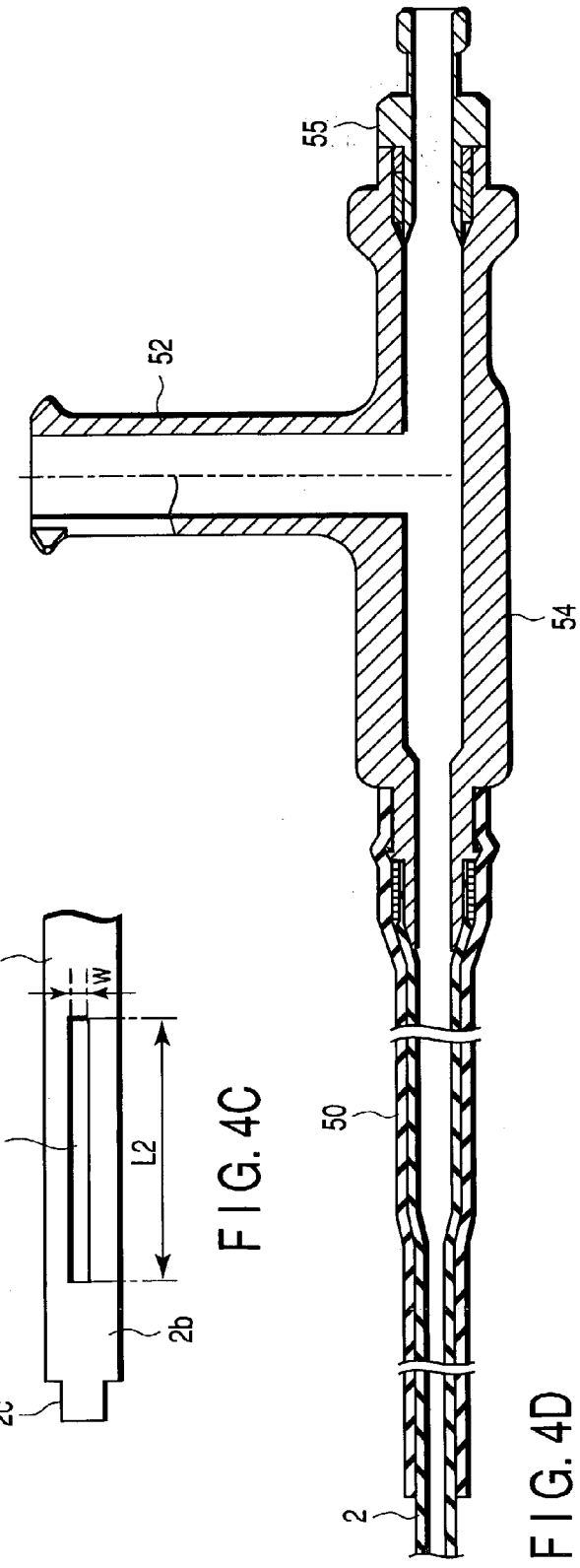
FIG. 4A
FIG. 4B
FIG. 4C
FIG. 4D

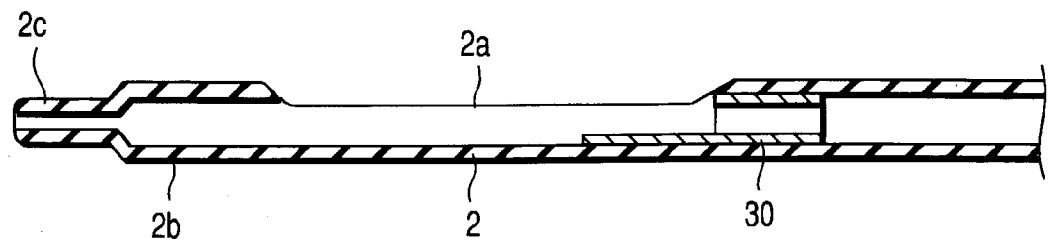
F I G. 11
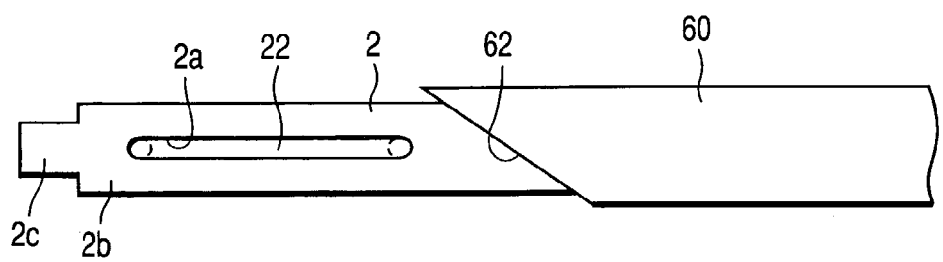
F I G. 12A
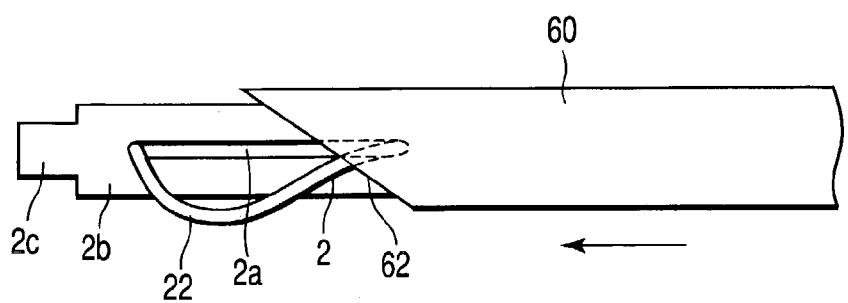
F I G. 12B

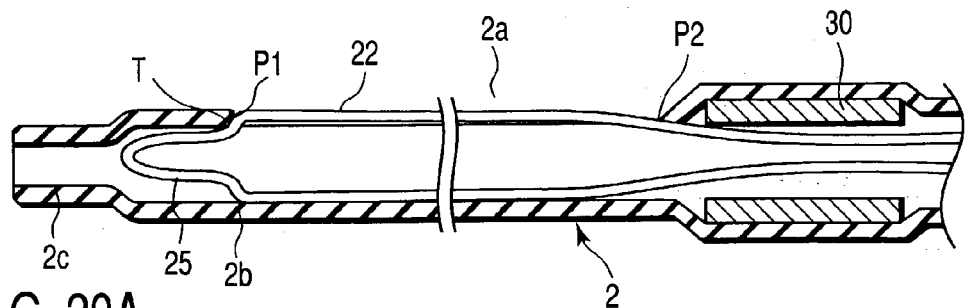
F I G. 20A
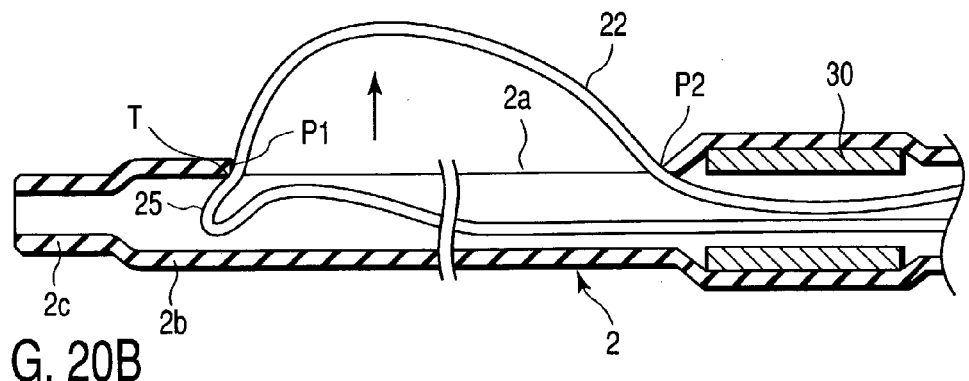
F I G. 20B
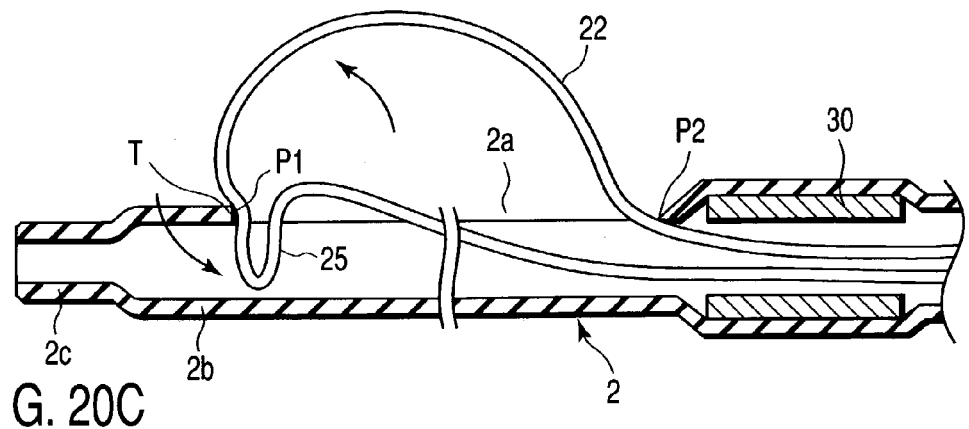
F I G. 20C
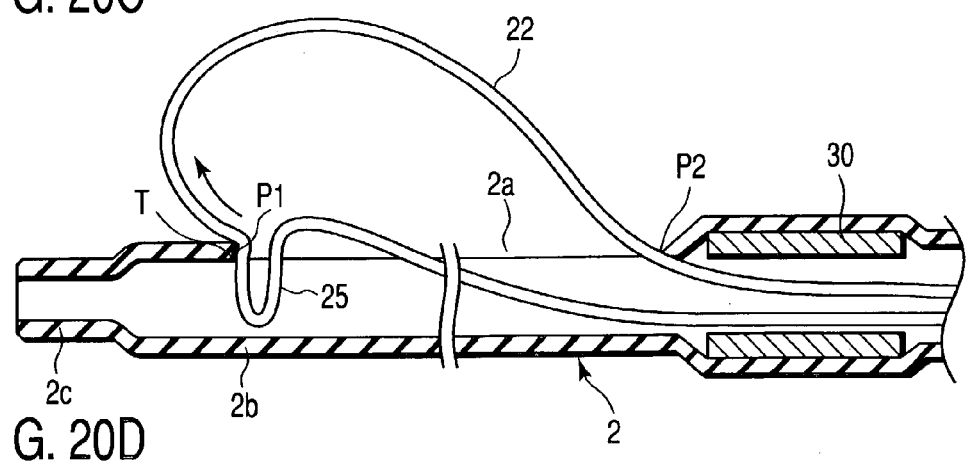
F I G. 20D

SURGICAL TREATMENT DEVICE

CROSS-REFERENCE TO RELATED APPLICATION

This application is based upon and claims the benefit of priority from the prior Japan Patent Applications No. 2002-239615 filed on Aug. 20, 2002, the entire contents of which are incorporated herein by reference.

BACKGROUND OF THE INVENTION

The present invention relates to a biotissue excising instrument used to excise biotissue using, for example, a high-frequency current.

A high-frequency snare has hitherto been known as biotissue excising instrument used to excise biotissue using a high-frequency current. The high-frequency snare is, for example, composed of a sheath 100 inserted endoscopically into a coelom through, for example, a treatment instrument insertion channel in an endoscope, a manipulation portion 102 provided at a proximal end of the sheath 100, a manipulation wire 104 inserted into the sheath 100 from the manipulation portion 102, and a slider 106 provided in the manipulation portion 102 to manipulate the manipulation wire 104 so as to advance and retreat freely, as shown in FIG. 26.

The manipulation wire 104 has a snare wire 110 at its leading end portion as a treatment portion that freely projects out of and sinks into an opening 100a in the leading end of the sheath 100. The snare wire 110 is shaped like a loop. It unfolds owing to its own recovery force when projected out of the opening 100a in the leading end of the sheath 100 when the slider 106 slides forward as shown in FIG. 26. Further, the snare wire 110 is compressed to reduce its own diameter when the slider 106 is slid toward an operator to pull part of the snare wire 110 into the sheath 100 via the manipulation wire 104 as shown in FIG. 27.

Accordingly, to excise biotissue, for example, a polyp using a high-frequency snare configured as described above, the snare wire 110 projected out of the opening 100a in the leading end of the sheath 100 and then unfolded is first caught on the polyp A as shown in FIG. 28A. Subsequently, in this caught state, the manipulation wire 104 is pulled toward the operator (the slider 106 is slid toward the operator) to reduce the diameter of the snare wire 110 as shown in FIG. 28B. Thus, the polyp A is bound tightly. In this tightly bound state, a high-frequency current is passed through the snare wire 110 to excise the polyp A.

All conventional high-frequency snares are of a frontward projecting type in which the snare wire 110 projects out of the opening 100a in the leading end of the sheath 100. Thus, when biotissue is excised using only this forward-projecting type of high-frequency snare, several problems may occur as described below.

That is, with the forward projecting type high-frequency snare, the snare wire 110 is continuously contracted by the inner surface of the sheath 100 until the snare wire 110 projects out of the opening 100a in the leading end of the sheath 100. Thus, the snare wire 100 is not opened until it is projected out of the opening 100a in the leading end of the sheath 100 by a certain distance by sliding the slider 106 of the manipulation portion 102 forward by a predetermined stroke. That is, with the forward projecting type high-frequency snare, the stroke of the slider 106 of the manipulation portion 102 cannot be used efficiently for the operation of increasing the diameter of the snare wire 110. Thus, the snare wire 110 cannot be linearly unfolded according to the stroke of the slider 106.

Further, with the forward projecting type high-frequency snare, the snare wire 100 must be unfolded with the leading end of the sheath 100 located in front of the polyp A and then allowed to approach the polyp A from above it so that the loop portion of the snare wire 100 is caught on the polyp A as shown in FIGS. 29A and 29B. However, the polyp A formed in the body does not always accommodate such an approach. It may be difficult to excise the polyp using the forward projecting type high-frequency snare depending on the manner of formation of the polyp.

Furthermore, with the forward projecting type high-frequency snare, rotation of the sheath 100 only causes the snare wire 100 to rotate around the axis of the sheath 100. Thus, in spite a change in the direction in which the loop is opened, the position of the snare wire 110 is not changed. Consequently, if the polyp A is located, for example, at the side of the snare wire 110 and it is difficult to allow the snare wire to approach the polyp A (direct the opening 100a in the leading end of the sheath 100 toward the polyp A), then the snare wire 110 cannot be caught on the polyp A. Therefore, it may be virtually impossible to carry out excision using the snare wire 110.

BRIEF SUMMARY OF THE INVENTION

It is an object of the present invention to provide a biotissue excising instrument which allows the efficient unfolding of a loop used to tightly bind biotissue and which allows the loop to easily approach biotissue that may be located in various directions.

The object of the present invention is accomplished by the biotissue excising instrument described below. That is, according to an aspect of the present invention, there is provided a biotissue excising instrument comprising a tubular sheath inserted into a body, a manipulator inserted into the sheath so as to advance and retreat freely through the sheath, and a treatment portion provided at a leading end of the manipulator and having a loop portion that can be unfolded and contracted to accommodate biotissue to be excised, wherein a slit is formed in a side of a leading end of the sheath to project and sink the loop portion of the treatment portion so that the manipulator is advanced or retreated to laterally project or sink the loop portion out of or into the sheath through the slit to unfold or contract the loop portion, thus excising biotissue in the loop portion.

BRIEF DESCRIPTION OF THE SEVERAL VIEWS OF THE DRAWING

FIG. 1A is a side sectional view of a sheath of a high-frequency snare according to an embodiment of the present invention;

FIG. 1B is a side view of a manipulation portion of the high-frequency snare according to this embodiment of the present invention;

FIG. 2A is an enlarged side view of a snare wire constituting the high-frequency snare in FIGS. 1A and 1B;

FIG. 2B is a side view showing a partial cross section of a manipulation wire to which the snare wire is connected;

FIG. 4A is a sectional view of a leading end side of the sheath constituting the high-frequency snare in FIGS. 1A and 1B;

FIG. 4B is a sectional view taken along line 4B—4B in FIG. 4A;

FIG. 4C is a view of the sheath as viewed from a direction 4A shown by an arrow in FIG. 4A;

FIG. 4D is a sectional view of a proximal end side of the sheath in FIG. 4A;

FIG. 11 is a sectional view showing a second variation of the sheath leading end portion;

FIGS. 12A and 12B are plan views showing first means for rotating an opening surface of the loop;

FIGS. 20A to 20D are sectional views showing, step by step, a series of unfolding operations of the loop portion according to a first aspect of the fifth variation of the sheath leading end portion;

DETAILED DESCRIPTION OF THE INVENTION

Figure 3A:
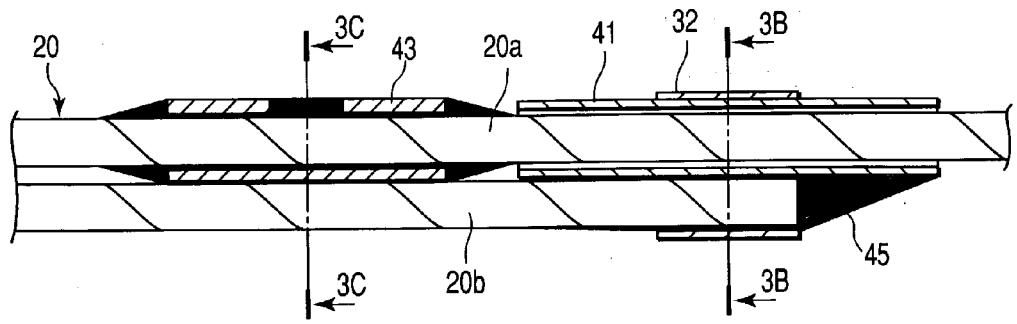
FIG. 3A is an enlarged sectional view of a part 3A of FIG. 2A.
Figure 3B:
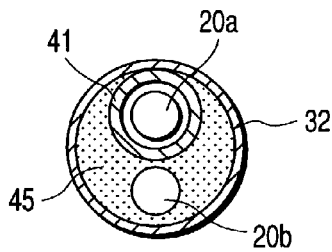
FIG. 3B is a sectional view taken along line 3B—3B in FIG. 3A.
Figure 3C:
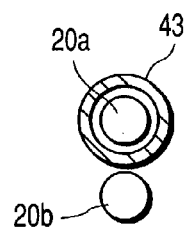
FIG. 3C is a sectional view taken along line 3C—3C in FIG. 3A.

An embodiment of the present invention will be described below with reference to the drawings.

FIGS. 1A to 6 show an embodiment of the present invention. FIGS. 1A and 1B show a high-frequency snare 1 as a biotissue excising instrument according to the present embodiment. As shown in the figures, the high-frequency snare 1 comprises a sheath 2 inserted endoscopically into a coelom through, for example, a treatment instrument insertion channel in an endoscope, and a manipulation portion 3 connected to a proximal end of the sheath 2. In this case, the sheath is formed of a flexible tube. A conductive manipulation wire (a manipulator) 4 is inserted into the sheath 2 from the manipulation portion 3 so as to advance and retreat freely through the sheath 2. The manipulation wire 4 also has a snare wire (treatment portion) 10 at its leading end portion, which freely projects out of and sinks into a side slit (an opening) 2a formed in a side of leading end of the sheath 2.

The manipulation portion 3 is comprised of a manipulation portion main body 7 and a slider 8 movably attached to the manipulation portion main body 7 to advance and retreat the manipulation wire 4. Further, a finger placement portion 9 is provided on the proximal end portion of the manipulation portion main body 7 and on the slider 8. Furthermore, the slider 8 is provided with an electrode cord connector 11. The electrode cord connector 11 is adapted to electrically connect to the manipulation wire 4 and to a high-frequency power supply 13 via an electrode code 16, the power supply providing a high-frequency current.

As shown in FIGS. 2A and 2B in detail, the snare wire 10 is shaped like a loop by folding a conductive wire 20. Specifically, the conductive wire 20 is folded so as to form a loop portion 22. Then, one end portion 20a of the conductive wire is waxed and fixed to the leading end of the manipulation wire 4. On the other hand, the other end portion 20b is waxed and fixed to a tubular slide member 32 located between the manipulation wire 4 and the loop portion 22.

The slide member 32 can slide through the sheath 2 together with the snare wire 10 as the manipulation wire 4 advances and retreats. As shown in the enlarged views in FIGS. 3A to 3C, the slide member 32 has an insertion tube 41 through which the one end portion 20a of the conductive wire 20 is inserted so as to advance and retreat freely through the tube. In the present embodiment, with the other end portion 20b of the conductive wire 20 and the insertion tube 41 positioned in an inner hole in the slide member 32, wax 45 is filled into the gaps between the members 20b and 32 and 41 to integrate the other end portion 20b of the conductive wire 20, the insertion tube 41, and the slide member 32 together (see FIG. 3B). Further, the one end portion 20a of the conductive wire 20 is inserted into the insertion tube 41 so as to advance and retreat freely through the tube.

Furthermore, a pipe 43 is fitted, waxed, and fixed around the outer periphery of the one end portion 20a of the conductive wire 20 located in front of the slide member 32. In this case, the outer diameter of the pipe 43 is set at such a value that it cannot pass through the inner diameter of the insertion tube 41.

Moreover, a bent convex portion 25 is formed at a leading end portion of the loop portion 22 corresponding to a turning point of the loop so as to project along the axial direction of the manipulation wire 4 within an opening surface 24 of the loop portion 22.

Further, as shown in FIG. 2B, a conductive rod 29 is waxed and fixed to the proximal end of the manipulation wire 4. A conductive connection portion 27 provided at the proximal end of the rod 29 is connected to the electrode cord connector 11, provided in the slider 8 of the manipulation portion 3.

As shown in FIGS. 4A to 4D in detail, the sheath 2 is formed as an elongated member consisting of resin material. It has a slit 2a in a side of its leading end, out of which the loop portion 22 of the snare wire 10 is projected. In this case, the shape and dimensions (width W and length L2 [see FIG. 4C] or their dimensional ratio) of the side slit 2a are set so that the loop portion 22 can be projected and unfolded stably without being twisted. In particular, the side slit 2a is an area that does not only support the unfolding loop portion 22 at its root but also has biotissue such as a polyp pressed against itself when the loop portion 22 is used to tightly bind the biotissue as described later. Furthermore, the side slit 2a is an area of the sheath 2 having a smaller strength because the sheath 2 is cut out in this area. Accordingly, if its shape and dimensions are set, considerations must be given to enable the side slit to stably support the loop portion 22, allow the side slit to resist being pressed against the biotissue, and avoid reducing the strength of the sheath 2. The length L2 of the side slit 2a is set depending on the previously described conditions and the size of the polyp to be excised.

Further, in the present embodiment, to compensate for the loss of strength of the sheath resulting from the formation of the side slit 2a, a collar member 30 is arranged so as to be fitted in the sheath 2 and extends from the proximal edge of the side slit 2a toward the proximal end of the sheath 2 by a predetermined length. The collar member 30 consists of, for example, a stainless steel pipe. When biotissue bound tightly by the loop portion 22 is pressed against the proximal edge of the side slit 2a, the collar member 30 resists the pushing force from the biotissue to prevent the slit 2a from being torn and the sheath 2 from being deformed. It also prevents the tightly bound biotissue from entering the sheath 2 (to prevent sheath 2 from being clogged with the biotissue).

Furthermore, a wire holding portion 2b is formed at the leading end of the sheath 2 to hold the leading end of the loop portion 22 while it is unfolding. A reduced diameter portion 2c is also formed at the leading end of the sheath 2 as a stopper against which the leading end of the loop portion 22 is abutted to prevent the loop portion 22 from projecting out of the leading end of the sheath 2. In this case, the wire holding potion 2b is formed of an area of the sheath 2 which is located in front of the side slit 2a. The inner diameter r and length L1 of the wire holding portion 2b are set so that a leading end portion of the snare wire 10 (loop portion 22) can be inserted easily into the wire holding portion 2b and held reliably by it (see FIG. 4A).

Moreover, the outer and inner diameters of the reduced diameter portion 2c are set to be smaller than those of other areas of the sheath 2 so as to form an opening 39 in the leading end surface of the sheath 2. In the present embodiment, the leading end of the reduced diameter portion 2c may be fully closed instead of forming the opening 39. However, the leading end of the reduced diameter portion 2c desirably has an opening in order to allow the sheath 2 to be washed properly.

Further, the proximal end portion of the sheath 2 is fixedly attached to a tubular member 54. A fold preventing tube 50 are fitted around the outer periphery of the connection area between the tubular member 54 and the sheath 2. Furthermore, the tubular member 54 is provided with a pipe sleeve 52 used to feed a liquid into the sheath 2 and a connection tube 55 connected to the manipulation portion 3.

In the present embodiment, the lengths of the wire 4 and sheath 2 and the stroke S of the slider 8 are set so that the loop portion 22 is opened (unfolded) maximally when the slider 8 is placed at the front end of its movement path, whereas the loop portion 22 sinks in an area closer to the operator (a proximal end of the sheath 2) than the collar member 30 (slit 2a) when the slider 8 is placed at the rear end of its movement path (the position shown by the alternate long and short dash line in FIG. 1B). Further, in the present embodiment, the sheath 2 is preferably reinforced with a metal mesh (blade) over its total length so that rotation of the sheath 2 enables the loop portion 22 to rotate (the direction in which the opening surface 24 of the loop portion 22 is opened changes), i.e., so that the rotating force of the manipulation portion 3 can be transmitted properly to the loop portion 22 via the sheath 2. In this case, as with generally known pressure-resistant hoses, the mesh is preferably embedded in the resin forming the sheath 2. Furthermore, the manipulation wire 4 is desirably formed of a solid wire consisting of material with a high torque transferability so that rotation of the wire 4 enables the loop portion 22 to rotate (the direction in which the opening surface 24 of the loop portion 22 is opened changes), i.e., so that the rotating force of the manipulation portion 3 can be transmitted properly to the loop portion 22 via the wire 4.

Now, description will be given of a case in which a polyp as biotissue is excised using the high-frequency snare 1 configured as described above.

First, with the leading end portion of the snare wire 10 (loop portion 22) held by the wire holding portion 2b so as to sink the loop portion 22 fully into the sheath (the loop portion 22 is not projected out of the side slit 2a), the sheath 2 is inserted into a treatment instrument insertion channel in an endoscope (not shown). Then, while using the endoscope for observation, the manipulation portion of the endoscope is manipulated to guide the leading end portion of the sheath 2 to the lateral neighborhood of the polyp (affected area).

Next, the slider 8 is slid forward to advance the manipulation wire 4. Then, since the snare wire 10, connected to the manipulation wire 4, has its leading end portion abutted against the reduced small portion 2c and held by the wire holding portion 2b, the loop portion 22 starts to project out of the side slit 2a in the sheath 2. That is, only the one end portion 20a of the conductive wire 20, connected to the manipulation wire 4, slides and unfolds like a loop out of the side slit 2a owing to its own recovery force. At this time, the loop portion 22 unfolds from the state shown by the solid line to the state shown by the broken line in FIG. 1 with the width of its root kept equal to the length L2 of the side slit 2a (with a predetermined loop diameter initially maintained). Further, because of the effects of shape and dimensions of the side slit 2a and the like, the loop portion 22 unfolds while being stably supported and without being twisted.

Figure 5A:
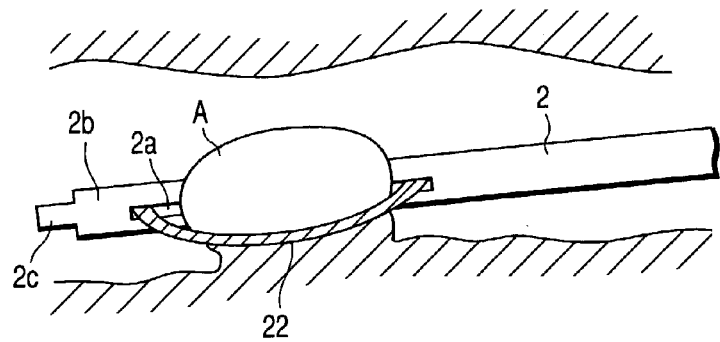
FIGS. 5A and 5B are sectional views showing a procedure of excising a polyp using the high-frequency snare in FIGS. 1A and 1B.

Furthermore, at this time, the opening direction of the opening surface 24 of the loop portion 22 is changed by, for example, rotating the sheath 2 or the manipulation wire 4, so that the opening surface 24 of the loop portion 22 lies opposite the polyp A. In this case, if the manipulation wire is formed of a solid wire or the sheath 2 is reinforced with a metal mesh, then the rotating force of the manipulation portion 3 can be transmitted easily to the loop portion 22. Accordingly, the opening surface 24 of the loop portion 22 can be placed opposite the polyp A easily. Then, the loop portion 22 unfolds until it becomes large enough to accommodate the polyp A. Then, the loop portion 22 is caught on the polyp A. This state is shown in FIG. 5A.

Figure 5B:
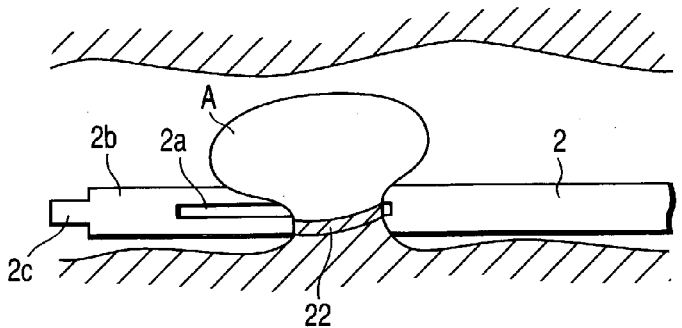
Figure 6:
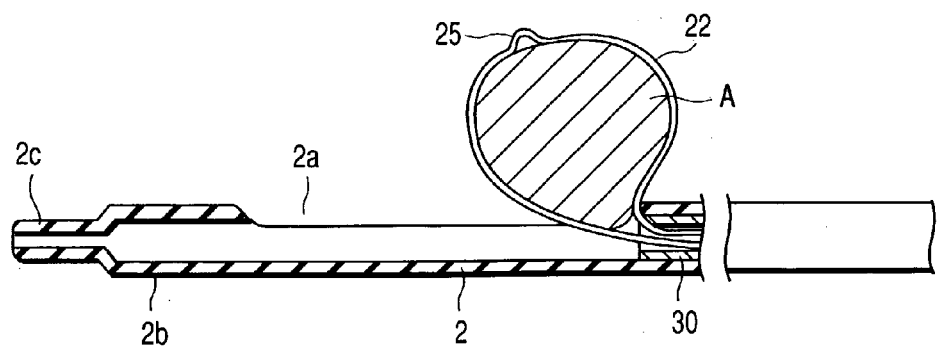
FIG. 6 is a sectional view showing how a polyp is bound tightly by a loop portion of the high-frequency snare in FIGS. 1A and 1B.

Once the loop portion 22 of the snare wire 10 is caught on the polyp A, the slider 8 is pulled toward the operator. Thus, the leading end portion of the loop portion 22 is released from the wire holding portion 2b to pull part of the loop portion 22 into the sheath 2. As shown in FIG. 5B, the loop portion 22 has its diameter reduced and tightly binds the polyp A. Then, the slider 8 is further slid toward the operator to press the polyp A, bound tightly by the loop portion 22, against the proximal edge of the side slit 2a as shown in FIG. 6. Subsequently, the high-frequency power supply 13 provides a high-frequency current to the snare wire 10 via the connector 11 to cut off the polyp A at the tightly bound part. At this time, even if the polyp A is pressed against the proximal edge of the side slit 2a, it is possible to prevent the slit 2a from being torn, the sheath 2 from being deformed, and the pressed polyp A from entering the sheath 2. This is because the collar member 30 as a reinforcing member is arranged at the proximal edge of the side slit 2a against which the polyp A is pressed. When the polyp A is cut off and the slider 7 moves to the rear end of its movement path (the position shown by the alternate long and short dash line in FIG. 1B), the loop portion 22 fully sinks in an area closer to the operator than the color member 30.

As described above, the high-frequency snare 1 as a biotissue excising instrument according to the present embodiment comprises the tubular sheath 2 inserted into a body, the manipulation wire 4 as a manipulator inserted into the sheath so as to advance and retreat through the sheath, and the snare wire 10 as a treatment portion provided at the leading end of the manipulation wire 4 and having the loop portion 22 that can be unfolded and contracted to accommodate biotissue to be excised. The high-frequency snare 1 is characterized in that the side slit 2a is formed in the side of the leading end of the sheath 2 to project and sink the loop portion 22 of the treatment portion so that the manipulation wire 4 is advanced or retreated to laterally project or sink the loop portion 22 out of or into the sheath 2 through the side slit 2a to unfold or contract the loop portion 22, thus excising biotissue in the loop portion 22.

Figure 7A:
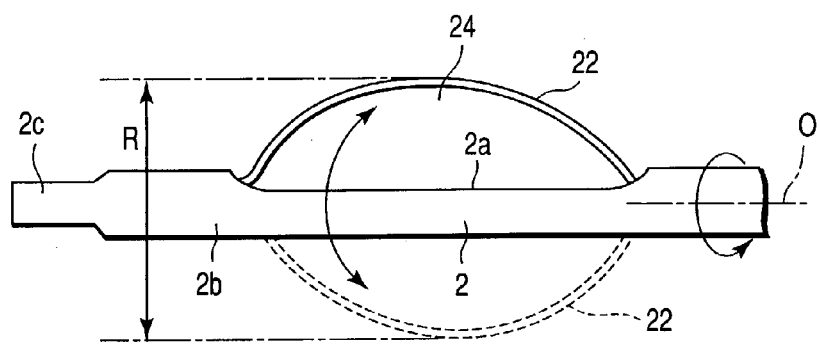
FIG. 7A is a schematic view showing how the loop portion of the high-frequency snare in FIGS. 1A and 1B is rotated.
Figure 7B:
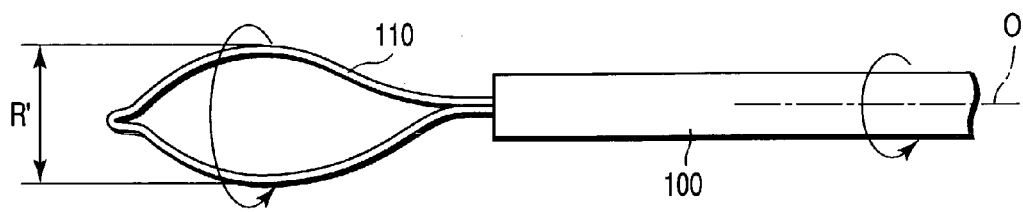
FIG. 7B is a schematic view showing how a loop portion of a conventional forward-projecting-type high-frequency snare is rotated.
Figure 26:
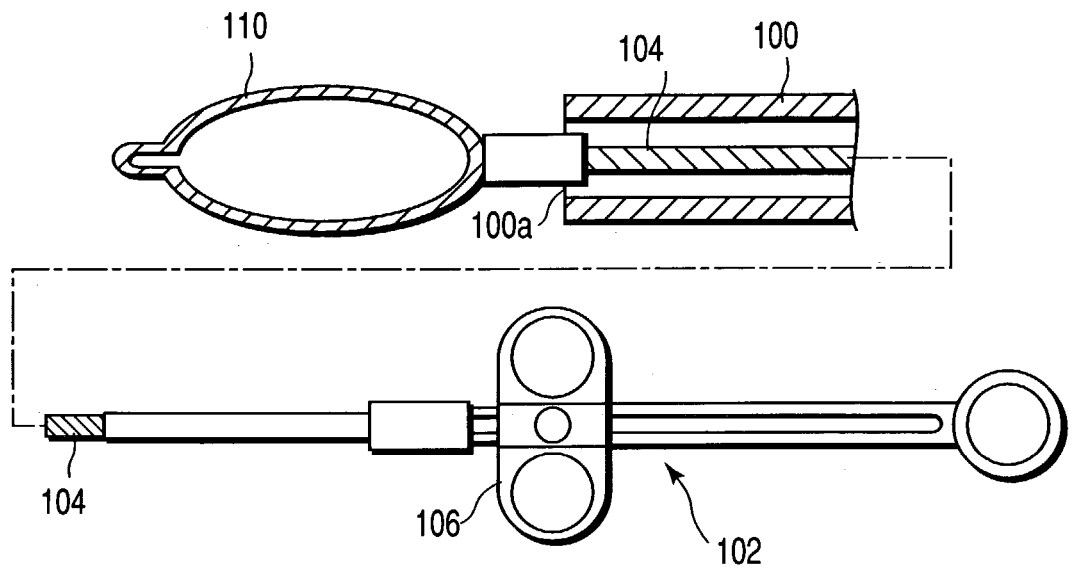
FIG. 26 is a schematic view showing a configuration of a conventional frontward-projecting-type high-frequency snare.
Figure 27:
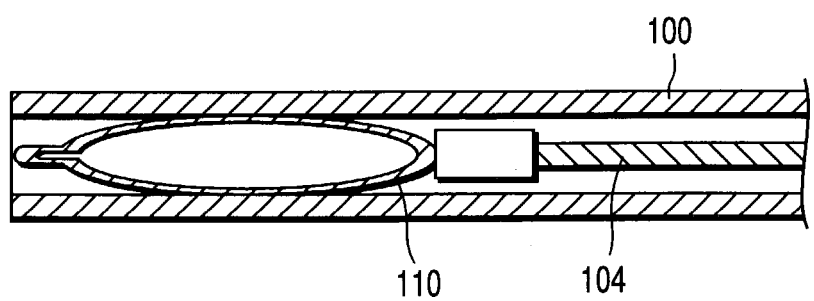
FIG. 27 is a sectional view of a leading end portion of the high-frequency snare in FIG. 26.
Figure 28A:
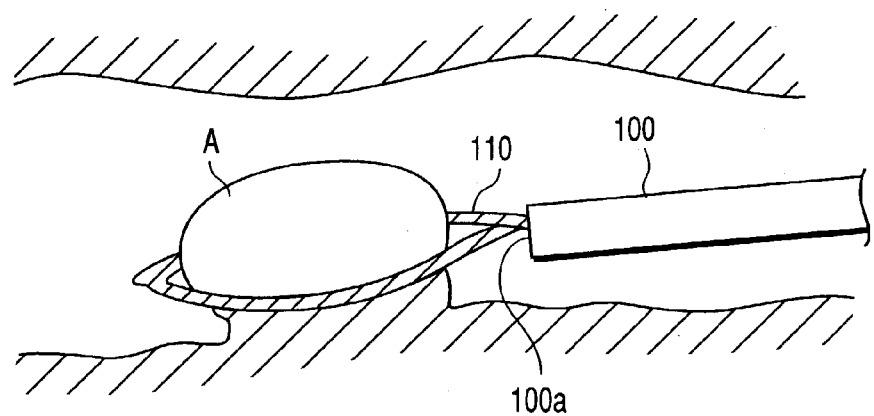
FIGS. 28A and 28B are sectional views showing a procedure of excising a polyp using the high-frequency snare in FIG. 26.
Figure 28B:
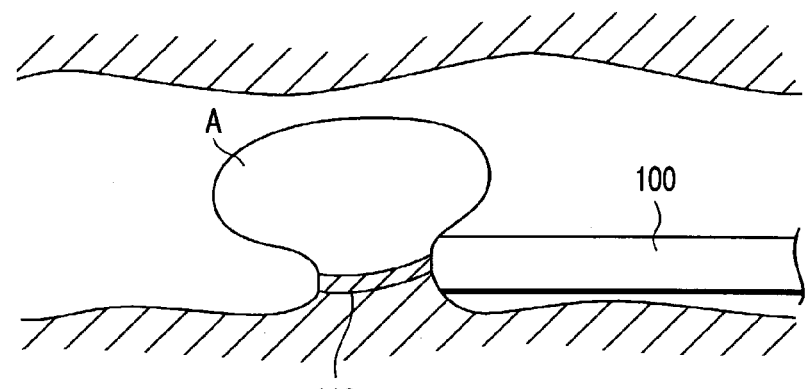
Figure 29A:
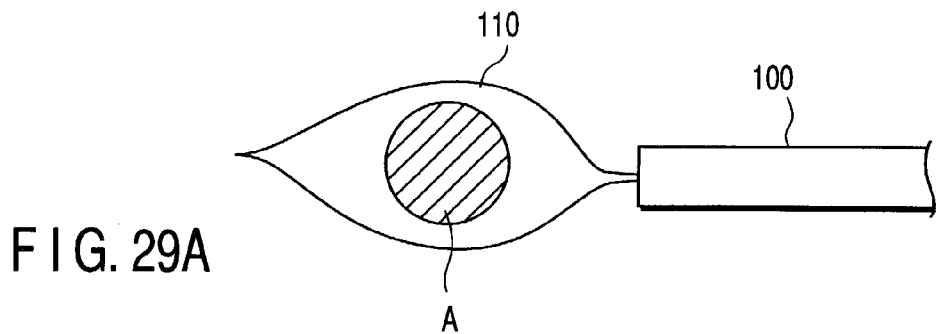
FIG. 29A is a plan view showing how the high-frequency snare in FIG. 26 is caught on the polyp.
Figure 29B:
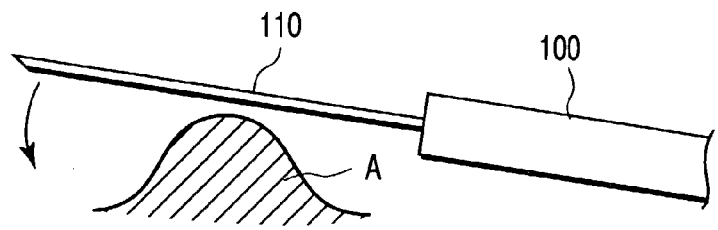
FIG. 29B is a side view of FIG. 29A.

Thus, by enabling the loop portion 22, which tightly binds biotissue (tissue to be excised), to project and sink at the side of the sheath 2, the loop portion 22 of the snare wire 10 can be caught easily on the tissue to be excised even if it is difficult to direct the leading end of the sheath 2 toward the tissue to be excised. In this case, when the sheath 2 is rotated, for example, around its axis 0 as shown in FIG. 7A, the loop portion 22 rotates over a wide range R from one end to the other end of the sheath 2 relative to the shaft 0. Not only the opening direction of the opening surface 23 but also its position (the position of the loop portion 22 in which the biotissue is accommodated) change. Consequently, the loop portion 22 is allowed easily to approach biotissue that may be located in various directions. In contrast, with the frontward-projecting type in which the snare wire (loop portion) 110 is projected out of the front of the sheath 100 (the type shown in FIG. 26), rotation of the sheath 100 only causes the snare wire 110 to rotate around the axis 0 of the sheath 100 (rotation range R') as shown FIG. 7B. Accordingly, in spite of a change in the opening direction of the loop, the position of the snare wire 110 remains unchanged. Consequently, substantially only the tissue located in front of the snare wire 110 (the projecting direction of the snare wire 110) can be excised.

Further, in the present embodiment, the loop portion 22 is unfolded or contracted by projecting only one side of the loop portion 22 out of the slit 2a, formed in the side of the sheath 2. Thus, compared to the forward-projecting-type high-frequency snare in which the loop diameter of the snare wire does not become large enough until the snare wire unfolds to some degree after projecting out of the opening in the leading end of the sheath, the loop portion 22 starts to unfold simultaneously with its own projection out of the slit 2a with the width of its root kept equal to the length L2 of the side slit 2a (with a predetermined loop diameter initially maintained). Further, in the present embodiment, the lengths of the wire 4 and sheath 2 and the stroke S of the slider 8 are set so that the loop portion 22 is opened maximally when the slider 8 is located at the front end of its movement path, whereas the loop portion 22 sinks in an area closer to the operator than the collar member 30 when the slider 8 is located at the rear end of its movement path (the position shown by the alternate long and short dash line in FIG. 1B). Accordingly, the stroke of the slider 8 can be used efficiently for the diameter increasing operation of the snare wire 10 (substantially all stroke of slider 8 of the manipulation portion 3 can be used for the diameter increasing operation of the snare wire 10). Consequently, the loop portion 22 of the snare wire 10 can be unfolded efficiently.

Figure 8:
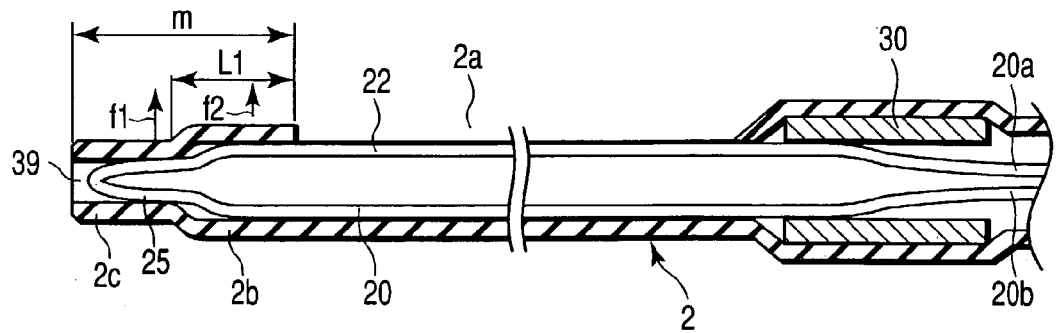
FIG. 8 is a sectional view showing a first variation of the sheath leading end portion (the loop portion is contracted)
Figure 9:
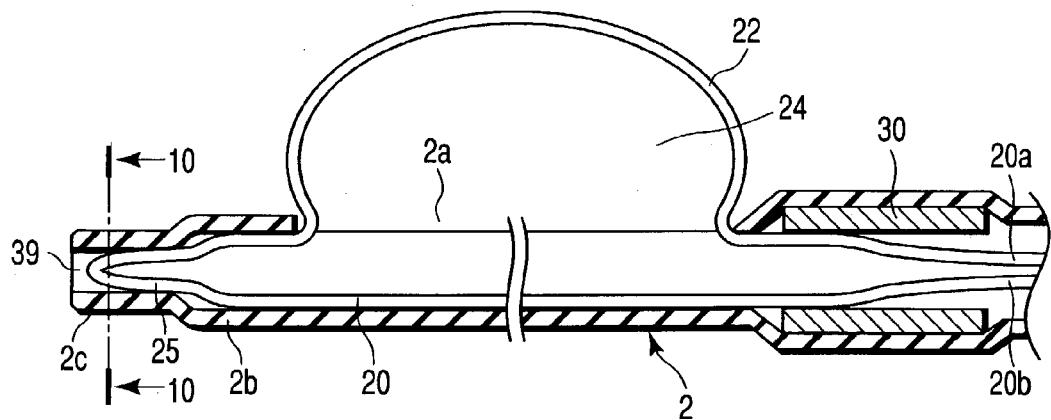
FIG. 9 is a sectional view showing the first variation of the sheath leading end portion (the loop portion is unfolded)
Figure 10:
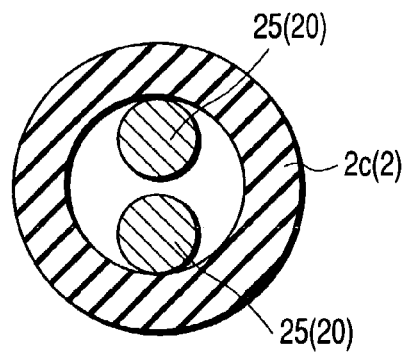
FIG. 10 is a sectional view taken along line 10—10 in FIG. 9.

In the present embodiment, the snare wire 10 (loop portion 22) is projected out of the side slit 2a and then unfolded by abutting its leading end portion against the reduced diameter portion 2c so as to be held by the wire holding portion 2*b*. However, as shown in FIGS. 8 and 9, the bent convex portion 25 at the leading end of the loop portion 22 may be fitted into the reduced diameter portion 2*c* so as to allow the leading end portion of the loop portion 22 to be held mainly by the reduced diameter portion 2*c* (see FIG. 8). In this state, the loop portion 22 may be projected out of the side slit 2*a* and then unfolded (see FIG. 9).

If the bent convex portion 25 is thus held by the reduced diameter portion 2*c*, the reduced diameter portion 2*c* must hold the bent convex portion 25 with such predetermined locking force that the loop portion 22 will not slip out of the side slit 2*a* while the loop portion 22 is unfolding. Specifically, the inner diameter of the reduced diameter portion 2*c* is set so that when the bent convex portion 25 at the leading end of the loop portion 22 is fitted into the reduced diameter portion 2*c*, the bent convex portion 25 has its diameter resiliently reduced (in this case, the bent convex portion 25 is contracted and deformed, for example, until the opposite portions of the conductive wire 20 which form the bent convex portion 25 are substantially parallel to each other), so that the resilient recovery force (reaction force) resulting from the decrease in diameter causes the bent convex portion 25 to be locked in the reduced diameter portion 2*c*. The inner diameter of the reduced diameter portion 2*c* is also set so that when the manipulation wire 4 is pulled to reduce the diameter of the loop portion 22 to tightly bind the polyp A, the bent convex portion 25 slips smoothly out of the reduced diameter portion 2*c*.

The inner diameter of the reduced diameter portion 2*c* is smaller than that of the wire holding portion 2*b*. Accordingly, the leading end portion of the loop portion 22 can be held with strong locking force compared to the use of the wire holding portion 2*b*. Then, by thus locking the bent convex portion 25 in the reduced diameter portion 2*c* to hold it, the leading end portion of the loop portion 22 is held mainly by the reduced diameter portion 2*c*. Thus, the wire holding portion 2*b* has only to lightly hold the leading end portion of the loop portion 22. (to illustrate this sensuously, in FIG. 8, the force of the loop portion 22 reacting to the holding force of the reduced diameter portion 2*a* is shown by a larger arrow f1, while the force of the loop portion 22 reacting to the holding force of the wire holding portion 2*b* is shown by a smaller arrow f2). Thus, the length L1 of the wire holding portion 2*b* can be minimized without reducing the total holding force. That is, the length L1 of the wire holding portion 2*b* can be reduced compared to the case in which the leading end portion of the loop portion 22 is held mainly by the wire holding portion 2*b*. Further, a decrease in the length L1 of the wire holding portion 2*b* serves to reduce the length m from the leading edge of the side slit 2*a* to the leading end of the sheath 2 (because it is possible to reduce the size of part of the sheath 2 which projects forward from the unfolding area [treatment area] of the loop portion). This allows the device to be manipulated easily in a narrow lumen.

Further, when the loop portion 22 is unfolded or contracted by projecting only one side of the loop portion 22 out of the slit 2*a*, formed in the side of the sheath 2 as in the present embodiment, if the length L2 of the side slit 2*a* is small, then an attempt to project more of the loop portion 22 out of the side slit 2*a* increases the curvature of the loop. Then, the force that increases the curvature of the loop acts on the wire 10 (20), thus twisting the loop 22. Thus, as previously described, in the present embodiment, the shape and dimensions (the width W and length L2 [see FIG. 4C] or their dimensional ratio) of the side slit 2*a* are set so that the loop portion 22 can be projected and unfolded stably without being twisted. Specifically, the width W of the slit 2*a* is reduced (the width must be slightly larger than the outer diameter of the wire 20) or the length L2 of the slit 2*a* is increased so as not to increase the loop curvature to the extent that the loop portion is twisted. However, if the length L2 or width W of the slit 2*a* is increased excessively, the strength of the sheath 2 decreases. In this case, part of the collar member 30 may be axially extended toward the slit 2*a* by a predetermined amount to increase the reinforced area as shown in FIG. 11. In this case, the collar member 30 can be used to change the hardness of the sheath 2 step by step. This prevents the hardness of the sheath 2 from changing rapidly because of the slit 2*a*, thus preventing the sheath 2 from being deformed when biotissue is bound tightly. Alternatively, to prevent the loop portion 22 from being twisted, it is contemplated that the wire 20 is formed of a solid wire. In this case, the wire 20 may have, for example, a rectangular cross section. It is also contemplated that the wire 20 may be formed of ultra-resilient alloy or may be provided with a tendency to bend so as to prevent twists on unfolding the loop.

Further, in the previously described embodiment, the opening direction of the opening surface 24 of the loop portion 22 is changed (the loop portion 22 is rotated) by rotating the sheath 2 or the manipulation wire 4. However, many other methods can be used to change the opening direction of the opening surface 24 of the loop portion 22. For example, as shown in FIGS. 12A and 12B, another tube 60 may be fitted around the outer periphery of the sheath 2 so as to advance and retreat freely. Then, the opening direction of the opening surface 24 of the loop portion 22 may be changed by pushing the tube 60 forward to change the direction in which the loop portion 22 projects out of the slit 2*a*. Specifically, the leading end surface of the tube 60 is formed as a slope 62 by cutting the tube 60 obliquely relative to the axial direction. Thus, when the tube 60 is moved forward, the loop portion 22 projecting out of the slit 2*a* is pushed against the slope 62. Then, the loop portion 22 is displaced (brought down) along the slope 62 to change the direction in which the loop portion 22 projects out of the slit 2*a* (see FIG. 12B). That is, as the tube 60 is further moved forward, the amount of change in the projecting direction of the loop portion 22 increases. Consequently, the opening direction of the opening surface 24 of the loop portion 22 changes more significantly.

Figure 13A:
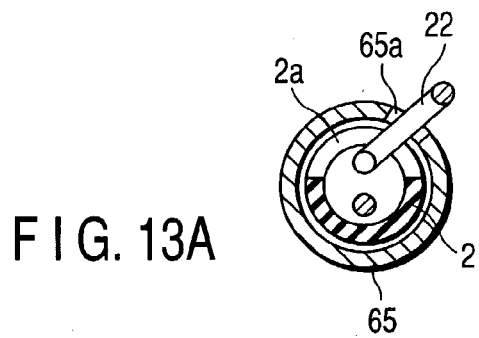
FIG. 13A is a sectional view taken along 13A—13A in FIG. 13B.
Figure 13B:
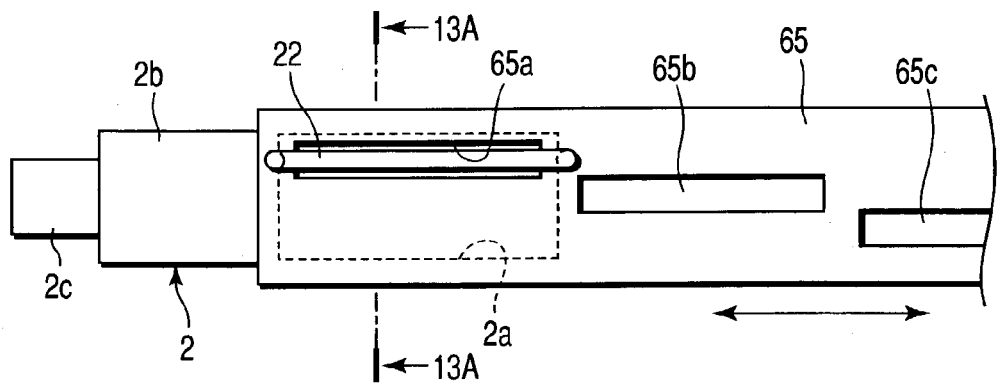
FIG. 13B is a plan view showing second means for rotating the opening surface of the loop.

Furthermore, FIGS. 13A and 13B shows another means for changing the opening direction of the opening surface 24 of the loop portion 22. That is, in this example, another tube 65 is fitted around the outer periphery of the sheath 2 so as to advance and retreat freely, the tube having a plurality of openings 65*a*, 65*b*, 65*c*, . . . that can be placed opposite the slit 2*a* in the sheath 2 from different directions. Specifically, the plurality of openings 65*a*, 65*b*, 65*c*, . . . , separated from one another along the axial direction, are formed in the tube 65 at different circumferential positions (they are separated from one another along the circumferential direction of the tube 65). Further, the slit 2*a* in the sheath 2 is formed to have such a width that the loop portion 22 can be projected in any directions in which the openings 65*a*, 65*b*, 65*c*, . . . are formed in the tube 65.

With such a configuration, the opening 65*a*, 65*b*, 65*c*, . . . that is opposite to the slit 2*a* in the sheath 2 can be changed (selected) simply by advancing or retreating the tube 65. The loop portion 22, projecting out of the slit 2*a*, projects laterally out of the tube 65 through one of the openings 65*a*, 65*b*, 65*c*, . . . which is opposite to the slit 2*a*. That is, with the present configuration, the projecting direction of the loop portion 22, projecting out of the slit 2a, can be changed by advancing or retreating the tube 65 to selectively place an arbitrary one of the openings 65a, 65b, 65c, . . . opposite the slit 2a.

In this example, the openings 65a, 65b, 65c, are separated from one another along the axial direction. However, the tube 65 may have only one opening, thereby, the projecting direction of the loop portion 22 may be changed by advancing the tube 65 to place the opening opposite the slit 2a and, in this state, rotating the tube 65 to change the direction in which the opening lies opposite the slit 2a.

Figure 14:
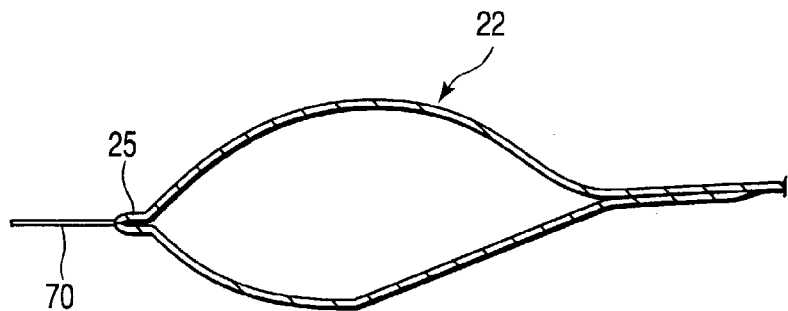
FIG. 14 is a plan view showing a variation of the loop portion.

FIG. 14 shows a variation of the loop portion 22. The loop portion 22 according to this variation has a guide portion 70 that can be inserted into an inner hole in the reduced diameter portion 2c of the sheath 2. In this case, the guide portion 70 extends axially forward from the bent convex portion 25 of the loop portion 22. With such a guide portion 70, after the polyp A has been bound tightly and then excised as shown in FIG. 6, the manipulation wire 4 can then be simply pushed in to allow the leading end of the loop portion 22 to be held by the wire holding portion 2b again, thus providing for the subsequent treatment. That is, simply by sliding the manipulation wire 4 forward without taking the sheath out of the body, the guide member 70 can be inserted into the inner hole in the reduced diameter portion 2c. Further, the guide member 70 can then be used to easily guide and set the leading end portion of the loop portion 22 so as to be held by the wire holding portion 2b.

In the present variation, the leading end portion of the loop portion 22 need not be held by the wire holding portion 2b provided that the guide member 70 is inserted into the reduced diameter portion 2c. That is, the wire holding portion 2b may be omitted. Further, even when the polyp A is bound tightly and excised as shown in FIG. 6, the guide member 70 may remain inserted into the inner hole in the reduced diameter portion 2c.

Figure 15:
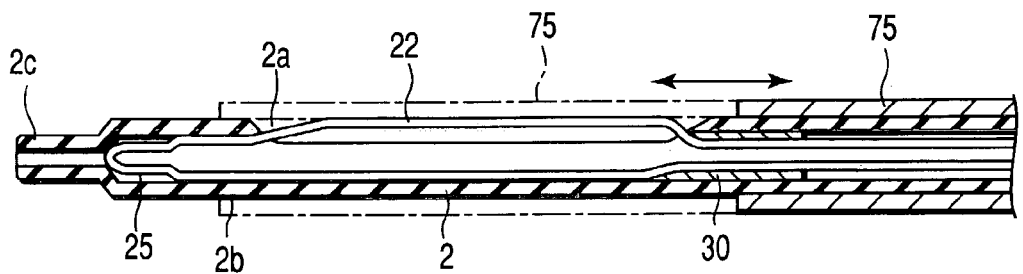
FIG. 15 is a sectional view showing a third variation of the sheath leading end portion.

FIG. 15 shows another means for more easily allowing the leading end portion of the loop portion 22 to be held by the wire holding portion 2b again. In general, after the leading end portion of the loop portion 22 has been released from the wire holding portion 2b, when the manipulation wire 4 is pushed in forward again to allow the leading end portion of the loop portion 22 to be held by the wire holding portion 2b, the loop portion 22 projects out of the side slit 2a and unfolds. Accordingly, it becomes difficult to allow the leading end portion of the loop portion 22 to be held by the wire holding portion 2b. Thus, in the example in FIG. 15, the tube 75 that can close the side slit 2a is slidably fitted around the outer periphery of the sheath 2. That is, if the leading end portion of the loop portion 22 is allowed to be held by the wire holding portion 2b again, the tube 75 may be slid forward to close the side slit 2a as shown by the alternate long and short dash line in FIG. 15. Then, even if the manipulation wire 4 is pushed in forward, the loop portion 22 does not project out of the side slit 2a or unfold. Consequently, it is possible to smoothly allow the leading end portion of the loop portion 22 to be held by the wire holding portion 2b. In this regard, any of these functions of the tube 75 may be provided using the previously described tube 60 or 65 (see FIGS. 12A, 12B, 13A, and 13B).

As another means for smoothly allowing the leading end portion of the loop portion 22 to be held by the wire holding portion 2b, a guide that directs the leading end of the loop portion 22 pushed out forward by the manipulation wire 4, toward the wire holding portion 2b may be provided, for example, close to the leading edge of the side slit 2a.

Figure 16A:
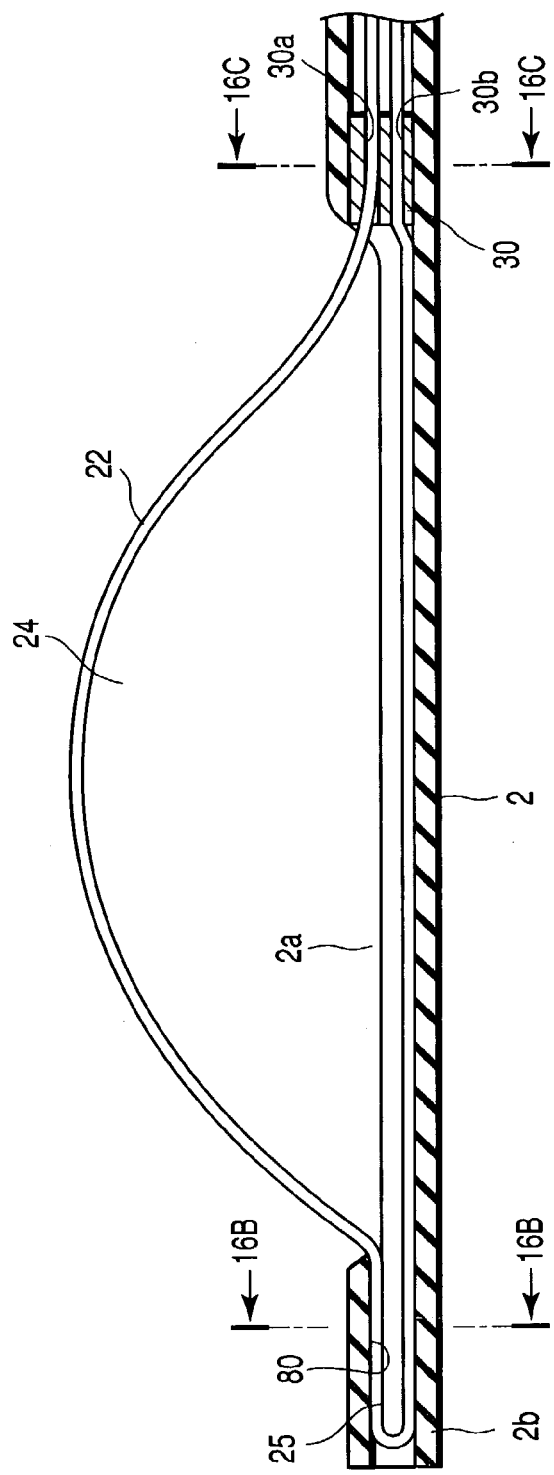
FIG. 16A is a sectional view showing a fourth variation of the sheath leading end portion.
Figure 16C:
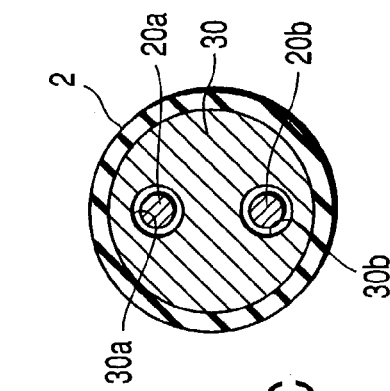
FIG. 16C is a sectional view taken along line 16C—16C in FIG. 16A.
Figure 16B:
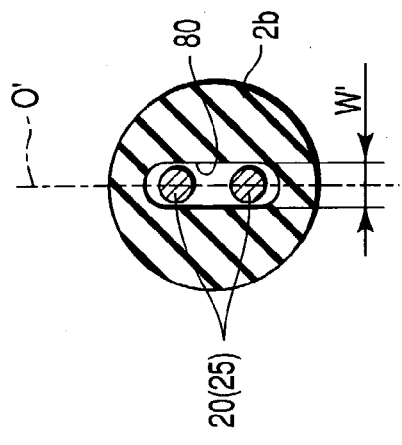
FIG. 16B is a sectional view taken along line 16B—16B in FIG. 16A.

FIGS. 16A to 16C show another means for preventing the loop portion 22 projecting out of the side slit 2a from being twisted. As shown in these figures, a slot 80 is formed in the wire holding portion 2b of the sheath 2 to hold the leading end portion of the loop portion 22. The slot 80 has a width W' substantially equal to the outer diameter of the conductive wire 20 and a major axis O' extending in the direction in which the opening surface 24 of the loop portion 22 extends. Further, the collar member 30 is provided with a pair of holes 30a and 30b through which the one end portion 20a and the other end portion 20b of the conductive wire 20, respectively, are inserted. These holes 30a and 30b have an inner diameter substantially equal to the outer diameter of the conductive wire 20.

With such a configuration, the loop portion 22 (opening surface 24) is held substantially within one surface owing to the pair of holes 30a and 30b in the collar member and the slot 80 in the wire holding portion 2b. This prevents the loop portion 22 projecting out of the side slit 2a from being twisted while unfolding.

Figure 17A:
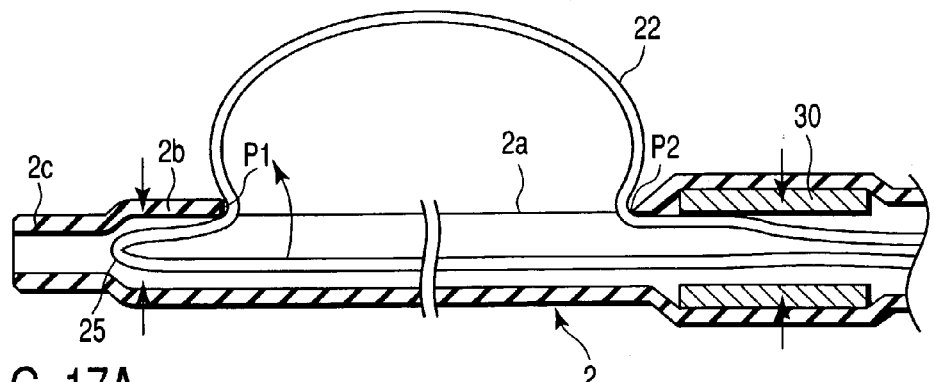
FIGS. 17A and 17B is a sectional view showing a comparison of a fifth variation of the sheath leading end portion with the above embodiment.

Thus, the twist of the loop portion 22 projecting out of the side slit 2a can be prevented by regulating the movement of the conductive wire 20 (holding the loop portion 22 substantially within one surface). In contrast, however, such twist can be prevented by allowing a large amount of the movement of the conductive wire 20 in a specified area. That is, in general, the loop portion 22 projecting out of the side slit 2a is twisted when the curvature radius of the loop decreases to cause the force that increases the curvature radius (the force that avoids bending) to act on the wire 10 (20). Specifically, as shown in FIG. 17A, when the loop portion 22 unfolds, it is pushed at two locations, i.e., the leading edge P1 and proximal edge P2 of the side slit 2a. The loop portion 22 is bent particularly significantly at the leading edge P1 to increase the bending reaction force on the leading end side. Thus, the curvature increases. Accordingly, the twist of the loop portion 22 can be effectively prevented by hindering the loop portion 22 from undergoing strong bending reaction force at the leading edge P1 of the side slit 2a while unfolding.

Figure 17B:
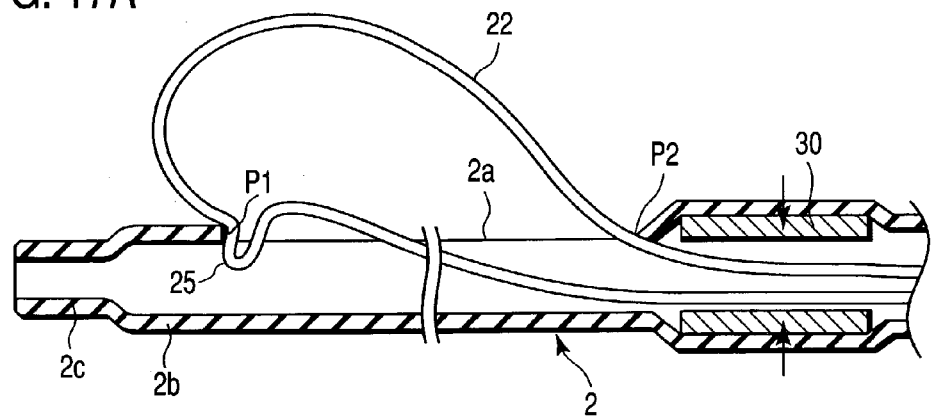
Figure 18:
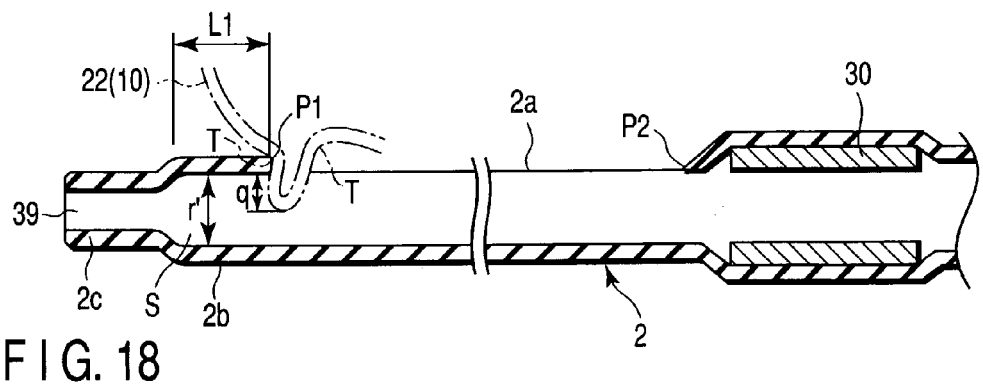
FIG. 18 is a sectional view showing the fifth variation of the sheath leading end portion.
Figure 19:
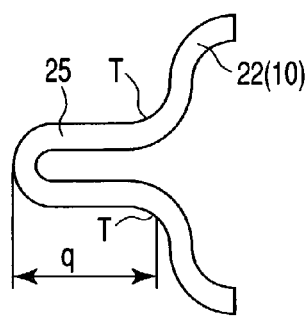
FIG. 19 is an enlarged view of a bent convex portion of the loop portion of the high-frequency snare.

As means for hindering the loop portion 22 from undergoing strong bending reaction force at the leading edge P1 of the side slit 2a, the loop portion 22 may be allowed to move freely at the leading edge P1 of the side slit 2a so as not to bend under strong pushing force from the leading edge P1 while unfolding (the proximal edge P2 is the only pushing portion contributing to bending the loop portion), as shown in FIG. 17B. Specifically, for example, as shown in FIG. 19, when the length of bent convex portion 25 of the loop portion 22 (the distance from the leading end of the loop portion 22 to a shoulder portion T of the bent convex portion 25) is defined as q, the inner diameter r' of the wire holding portion 2b is set to be equal to or larger than q ($r' \geq q$) as shown in FIG. 18. Thus, while the loop is unfolding, the leading end portion (bent convex portion 25) of the loop portion 22 can rotate freely within an internal space S of the wire holding portion 2b around the shoulder portion T, which rests against the leading edge P1.

In this case, to reliably rest the shoulder portion T of the loop portion 22 against the leading edge P1 of the side slit 2a before the loop unfolds, the length L1 of the wire holding portion 2b is preferably set to be substantially equal to the length q of the bent convex portion 25. However, actually, even if the length q of the bent convex portion 25 is smaller than the length L1 of the wire holding portion 2b, the shoulder portion T of the loop portion 22 engages with the leading edge P1 of the side slit 2a while the loop portion 22 is unfolding. This enables the loop portion 22 to unfold as shown in FIG. 17B. To clarify this point, separate and step-by-step description will be given of an unfolding operation performed by the loop if the length L1 of the wire holding portion 2b is substantially equal to the length q of the bent convex portion 25, and of an unfolding operation performed by the loop if the length q of the bent convex portion 25 is smaller than the length L1 of the wire holding portion 2b.

FIGS. 20A to 20D show, step by step, the unfolding operation performed by the loop if the length L1 of the wire holding portion 2b is substantially equal to the length q of the bent convex portion 25. First, as shown in FIG. 20A, when the leading end portion of the loop portion 22 is allowed to be held by the wire holding portion 2b, the shoulder portion T of the loop portion 22 substantially automatically rests against the leading edge P1 of the side slit 2a. In this state, when the manipulation wire 4 is advanced, the loop portion 22, connected to the manipulation wire 4, starts to project out of the side slit 2a in the sheath 2 because its leading end portion has been abutted against the reduced diameter portion 2C and held by the wire holding portion 2b. At this time, the leading end portion of the loop portion 22 rotates around the shoulder portion T resting against the leading edge P1, as shown in FIG. 20B (the bent convex portion 25 rotates within the internal space S of the wire holding portion 2b around the shoulder portion T). In this initial stage of rotation, as shown by arrows in FIG. 20B, the loop portion 22 unfolds upward and backward. However, as the loop portion 22 further unfolds to further rotate its leading end portion around the shoulder portion T, the bent convex portion 25 is directed downward as shown in FIGS. 20C and 20D. Then, the loop portion 22 starts to unfold upward and forward rather than upward and backward. Even in this case, the shoulder portion T engages with the leading edge P1, thus preventing the loop portion 22 from entirely slipping out of the sheath 2 through the side slit 2a.

Provided that the leading end portion of the loop portion 22 can thus rotate freely around the shoulder portion T, which rests against the leading edge P1 of the side slit 2a (provided that the leading end portion of the loop portion 22 can be provided with a larger degree of freedom) on unfolding, it is impossible that the unfolding loop portion 22 bends under strong pushing force from the leading edge P1. This serves to reduce the bending reaction force to effectively prevent the loop portion 22 from being twisted.

Figure 21A:
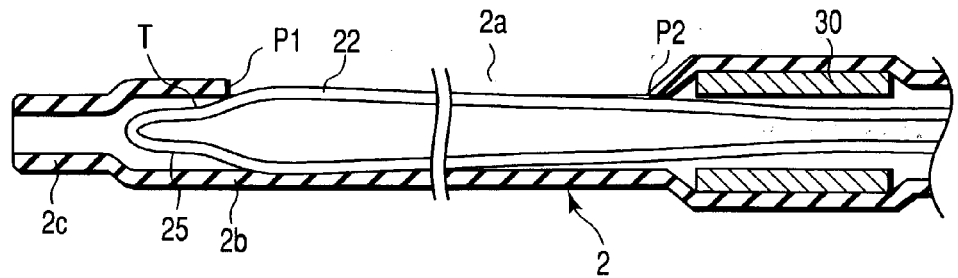
FIGS. 21A to 21E are sectional views showing, step by step, a series of unfolding operations of the loop portion according to a second aspect of the fifth variation of the sheath leading end portion.
Figure 21B:
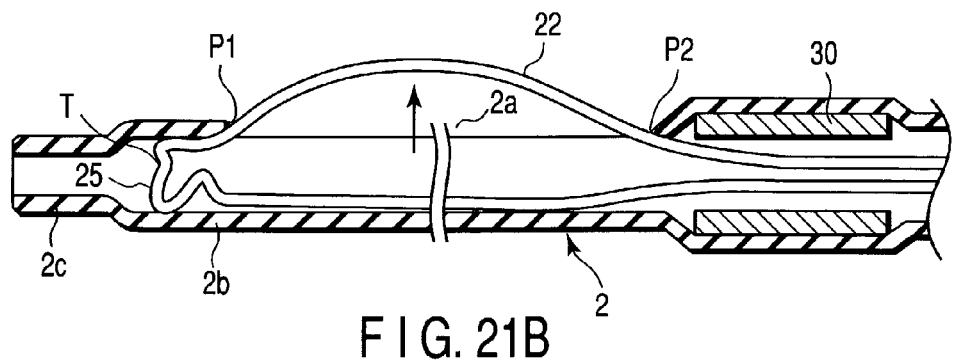
Figure 21C:
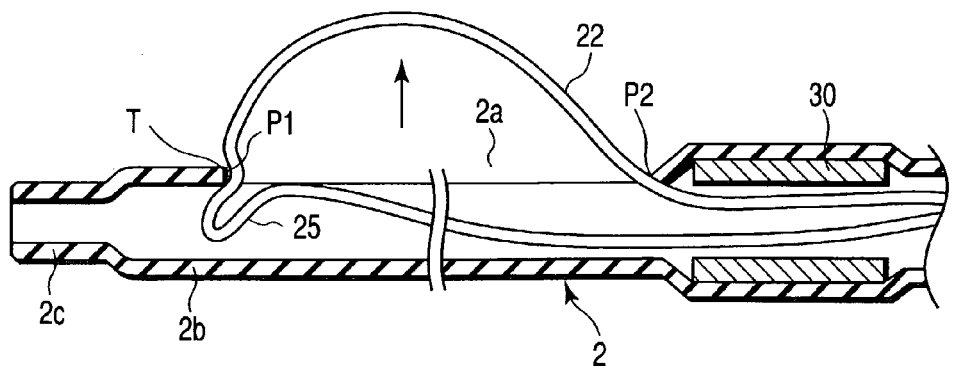
Figure 21D:
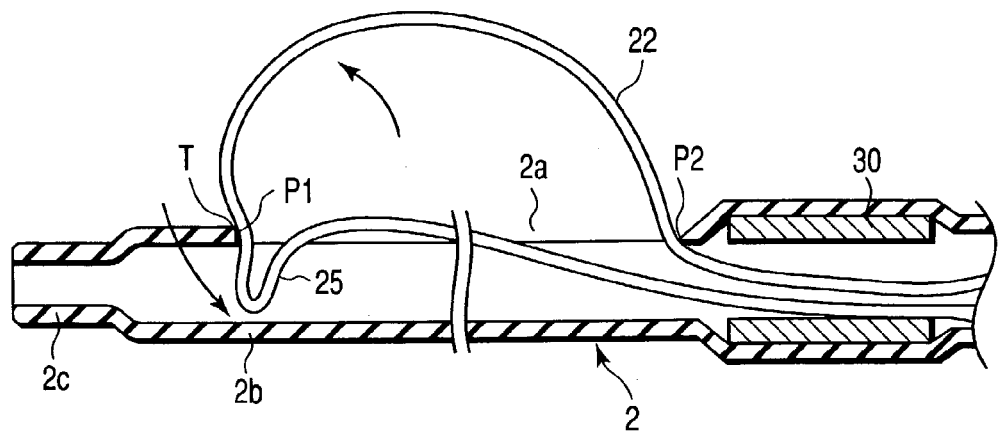
Figure 21E:
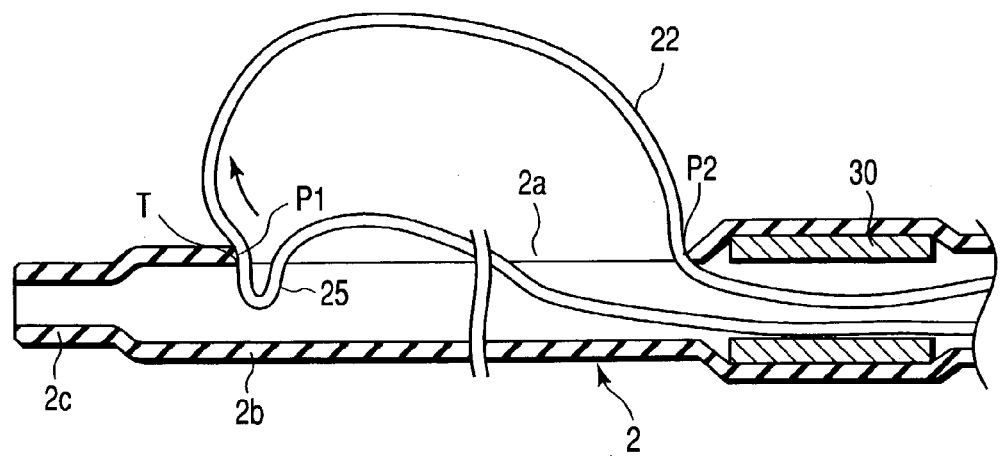

FIGS. 21A to 21E show, step-by-step, the unfolding operation performed by the loop if the length q of the bent convex portion 25 is smaller than the length L1 of the wire holding portion 2b. First, as shown in FIG. 21A, when the leading end portion of the loop portion 22 is allowed to be held by the wire holding portion 2b, the shoulder portion T of the loop portion 22 sinks completely into the wire holding portion 2b. Then, in this state, when the manipulation wire 4 is advanced, the loop portion 22 projects out of the side slit 2a in the sheath 2 and starts to unfold as shown in FIG. 21B. At this time, the loop portion 22 unfolds upward and backward. Accordingly, the shoulder portion T of the loop portion 22 slips out of the wire holding portion 2b and rests against and engages with the leading edge P1 of the side slit 2a as shown in FIG. 21C. Then, the leading end portion of the loop portion 22 starts to rotate around the shoulder portion T. Subsequently, as described in FIGS. 20B to 20D, the leading end portion continues to rotate so as to direct the bent convex portion 25 downward. Thus, the loop portion 22 starts to unfold upward and forward rather than upward and backward (see FIGS. 21D and 21D).

Figure 22A:
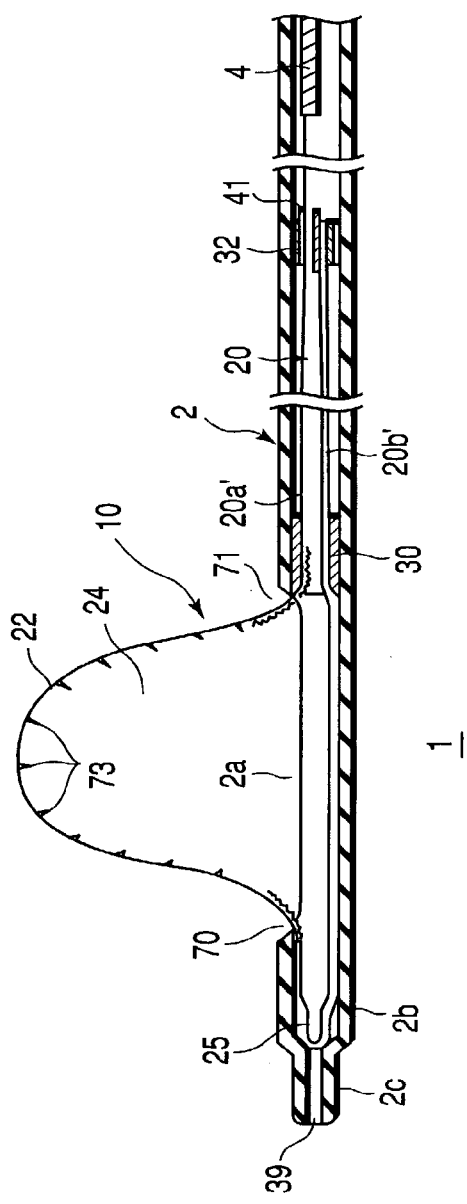
FIG. 22A is a side sectional view of a sheath of a high-frequency snare according to a variation.
Figure 22B:
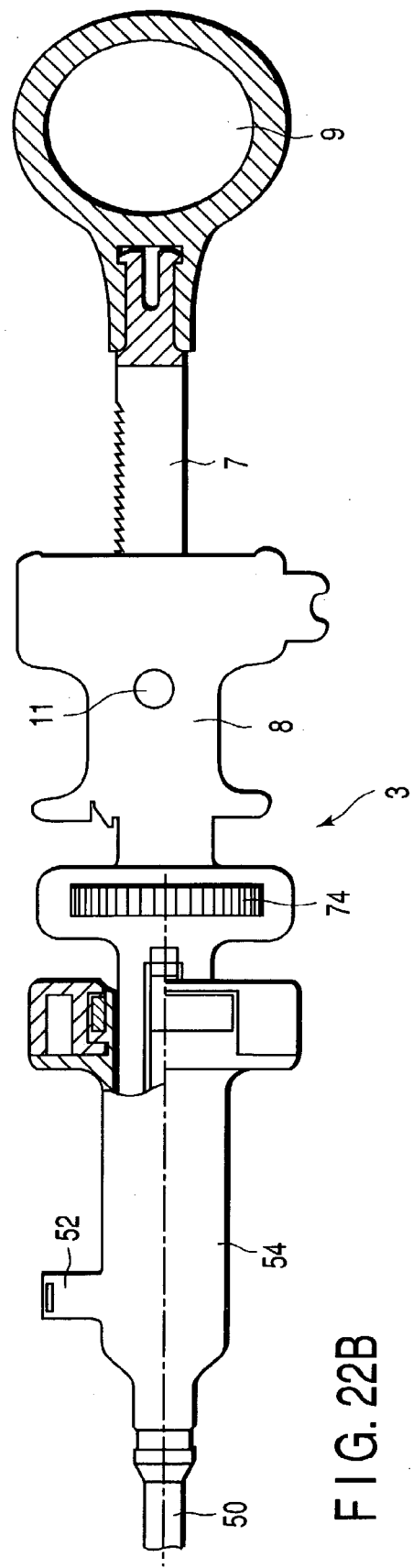
FIG. 22B is a side view of a manipulation portion of the high-frequency snare in FIG. 22A.

FIGS. 22A and 22B show a variation of the high-frequency snare 1. As shown in these figures, in this variation, the conductive wire 20 of the snare wire 10 is composed of a hard first wire portion 20b' and a second wire portion 20a' which is softer than the first wire portion 20b' and which has a smaller diameter than the first wire portion 20b'. The first wire portion 20b' has one end secured to the slide member 32 and the other end turned up so as to form the bent convex portion 25. On the other hand, the second wire portion 20a' has one end secured to the manipulation wire (multiple wires or torque wire) 4 and the other end secured to the first wire portion 20b'. The manipulation wire 4 is electrically connected to the electrode cord connector 11, provided in the slider 8. It is also fixed to a rotator 74 provided in the manipulation portion 3 so that it can rotate with the rotator 74.

Further, in the second wire portion 20a', at least one needle or projection-like non-slip chip 73 is formed inside the opening surface 24 of the loop portion 22. Furthermore, the second wire portion 20a' is provided with a tendency to bend in its predetermined areas. Specifically, the second wire portion 20a' is provided with a tendency to bend in such a direction as resists the twist of the loop portion, in its areas 70 and 71 that cross the leading and proximal edges, respectively, of the side slit 2a immediately before the loop portion 22 starts to be twisted after projecting out of the side slit 2a (the state shown in FIG. 22A)(the areas provided with the tendency to bend are shown by the wavy lines in the figure).

Thus, in the present variation, the first wire portion 20b' is formed to be hard (have a large diameter), while the second wire portion 20a' is formed to be soft and to have a smaller diameter. Further, the second wire portion 20a' is provided with the tendency to bend in its areas 70 and 71. This effectively suppresses the twist of the loop portion 22 projecting out of the side slit 2a. Furthermore, even if the loop portion 22 is twisted, its twist can be easily cleared by rotating the rotator 74 and thus the manipulation wire 4.

Moreover, in the present variation, the at least one needle or projection-like non-slip chip 73 is formed inside the opening surface 24 of the loop portion 22. Accordingly, when the loop portion 22 is caught on the polyp A, the chip 73 cuts into the polyp A to prevent the loop portion 22 from slipping. Consequently, the loop portion 22 can be reliably caught on the polyp A to tightly bind it. In the present variation, to prevent the sheath 2 from slipping on the polyp A, the sheath 2 may be provided with non-slip means around the outer periphery of its leading end portion, located opposite the polyp A. Such non-slip means may be formed by, for example, making cuts like meshes or knurls in the outer peripheral surface of the sheath 2.

Figure 23A:
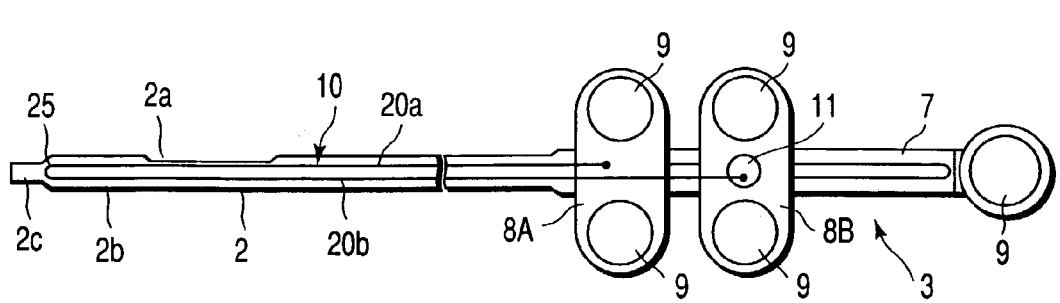
FIGS. 23A to 23C are schematic views showing variations of the manner in which the loop portion projects out of a side slit using a slider.
Figure 23B:
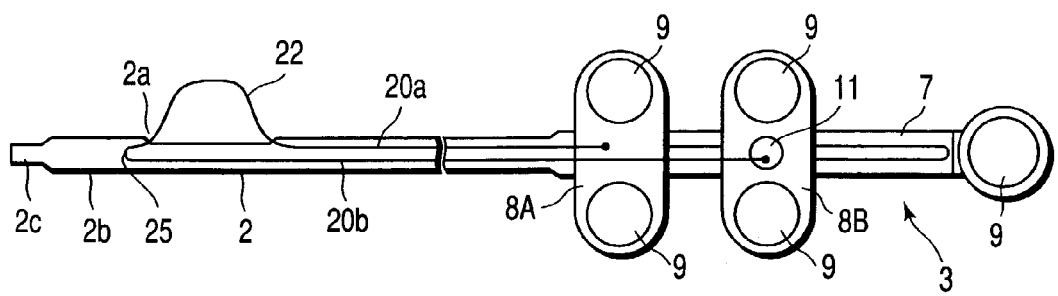
Figure 23C:
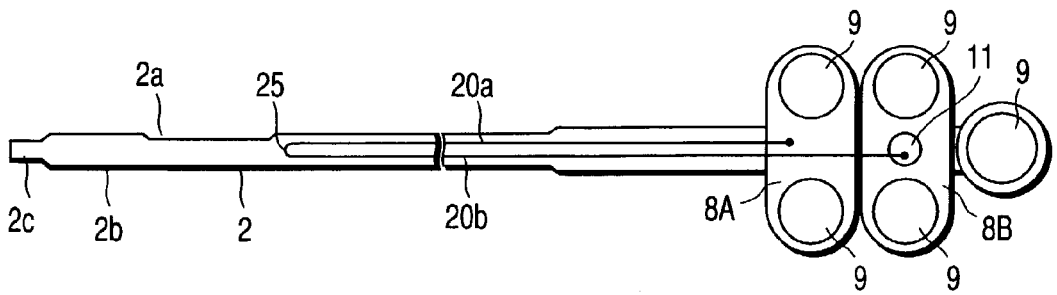

FIGS. 23A to 23C show a variation of the manner in which the loop portion 22 is projected out of the side slit 2a using the slider 8. As shown in these figures, in the present variation, the manipulation portion 3 is provided with two sliders 8A and 8B. The loop portion 22 can be projected out of the side slit 2a by moving the sliders 8A and 8B relative to each other. Specifically, the one end portion 20a of the conductive wire 20, forming the snare wire 10, is connected to the first slider 8A, located in the front. On the other hand, the other end portion 20b of the conductive wire 20 is electrically connected to the electrode cord connector 11 of the second slider 8B, located in the rear.

With such a configuration, if the loop portion 22 is to be projected out of the side slit 2a, then first, in the state shown in FIG. 23A, i.e., with the leading end of the snare wire 10 abutting against the reduced diameter portion 2c, only the second slider 8B is slid toward the operator. This state is shown in FIG. 23B. At this time, due to the bent convex portion 25, the other end portion 20b of the conductive wire 20 is pulled back toward the operator, while the one end portion 20a of the conductive wire 20 is not pulled back toward the operator. Accordingly, the one end portion 20a of the conductive wire 20a projects out of the side slit 2a by an amount corresponding to the above difference (the amount by which the other end portion 20b of the conductive wire 20 is pulled back). Further, in the state shown in FIG. 23B, when the first slider 8A is slid toward the operator, the loop portion 22 can be pulled into the sheath 2. This state is shown in FIG. 23C.

Consequently, this loop portion projecting manner also makes it possible to carry out a polyp excision procedure similar to that in the previously described embodiment.

FIGS. 24A to 25E show a method of utilizing the twist of the loop portion 22 to catch the loop portion 22 on the polyp A from its front or rear to tightly bind it.

Figure 24A:
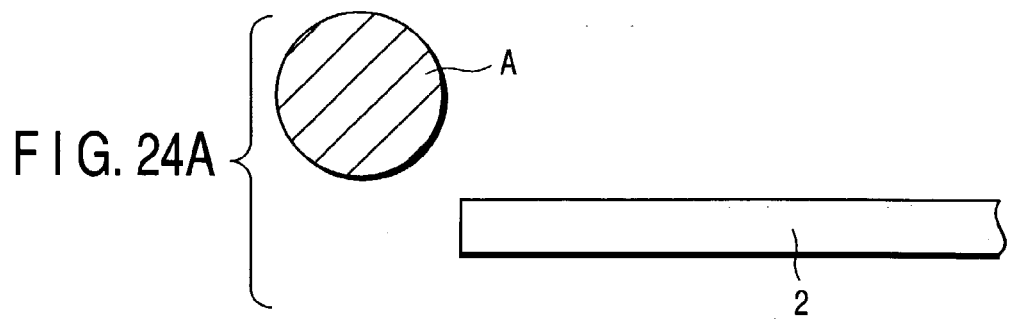
FIG. 24A is a schematic view showing a first step of a method of catching the loop portion on a polyp from its front and tightly binding the polyp.
Figure 24B:
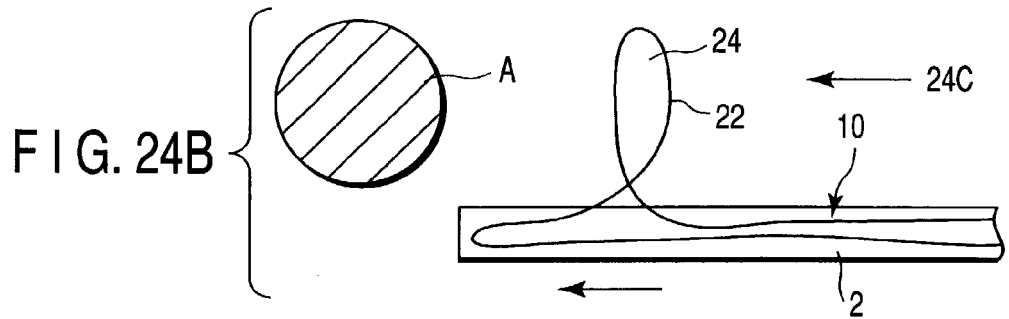
FIG. 24B is a schematic view showing a second step succeeding the first step in FIG. 24A.
Figure 24D:
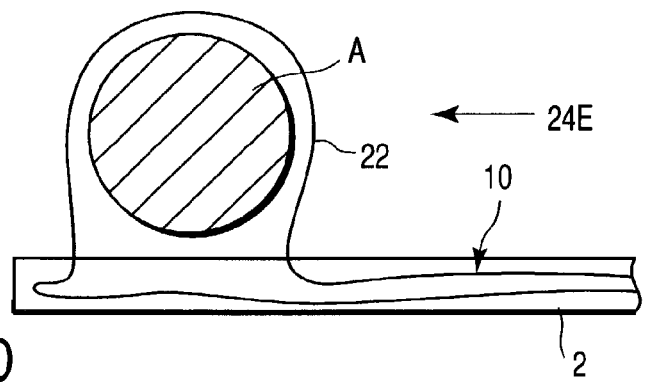
FIG. 24D is a schematic view showing a third step succeeding the second step in FIG. 24B.
Figures 24C, 24E:
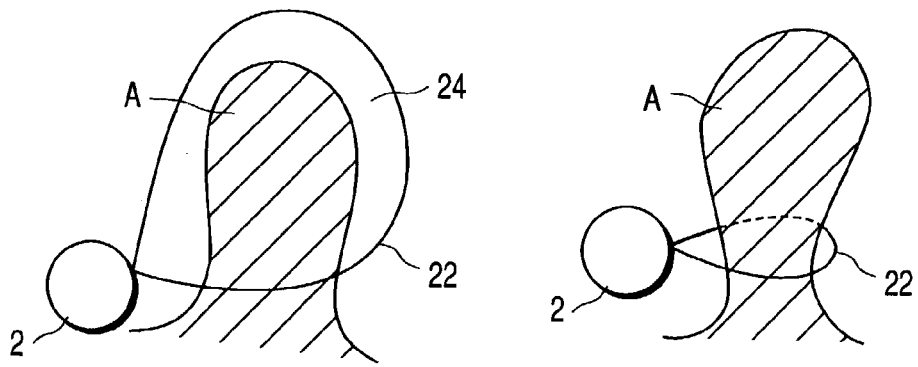
FIG. 24C is a view showing the second step as viewed from the direction 24C in FIG. 24B.
FIG. 24E is a view showing the third step as viewed from the direction 24E in FIG. 24D.

FIGS. 24A to 24E show a method of catching the loop portion 22 on the polyp A from its front to tightly bind it. Specifically, first, as shown in FIG. 24A, the leading end of the sheath 2 is placed in front of and at the side of the polyp A. In this state, the loop portion 22 is projected out of the side slit 2a. The loop portion 22 is also twisted to the degree that its opening surface 24 is not completely closed, so as to place the opening surface 24 in front of and opposite the polyp A. This state is shown in FIGS. 24B and 24C. Then, in this state, the sheath 2 is advanced at the side of the polyp A. Then, the loop portion 22 can be caught on the polyp A as shown in FIGS. 24D and 24E.

Figure 25A:
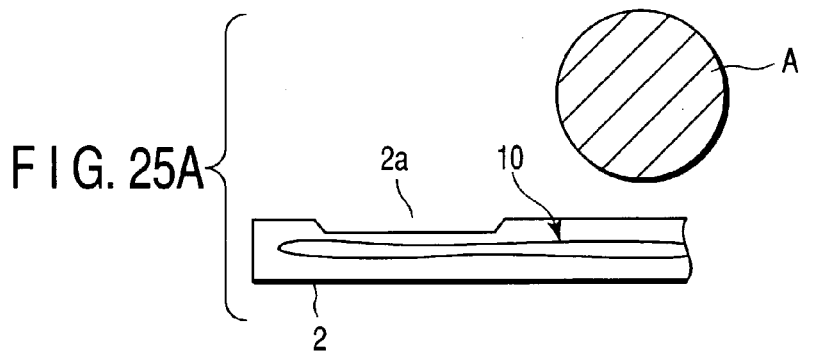
FIG. 25A is a schematic view showing a first step of a method of catching the loop portion on a polyp from its rear and tightly binding the polyp.
Figure 25B:
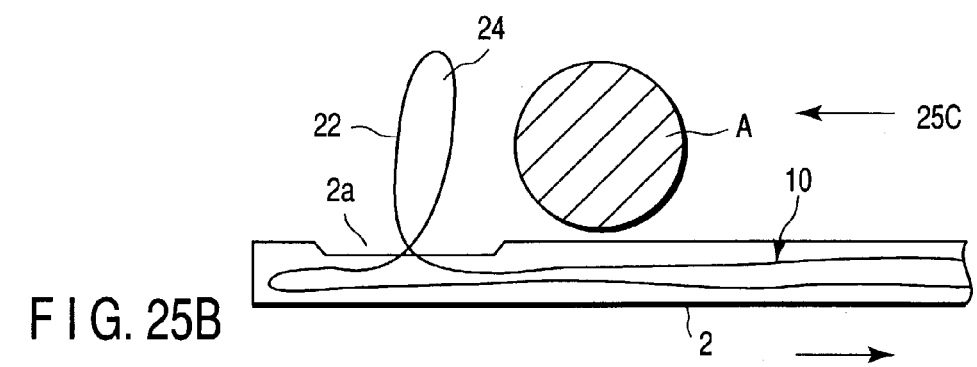
FIG. 25B is a schematic view showing a second step succeeding the first step in FIG. 25A.
Figure 25D:
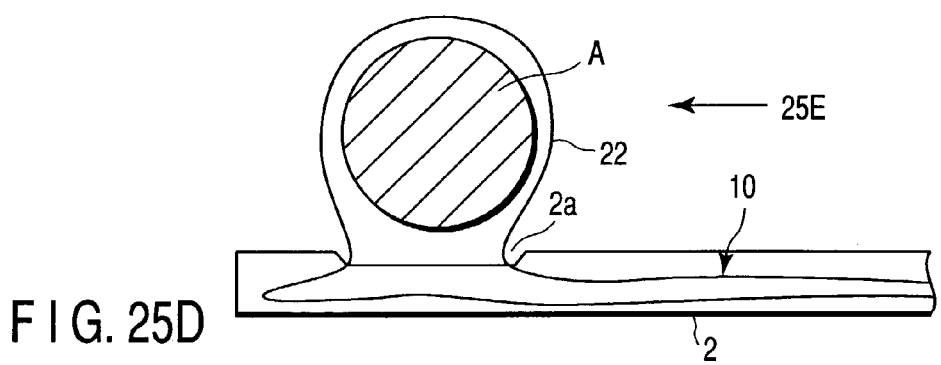
FIG. 25D is a schematic view showing a third step succeeding the second step in FIG. 25B.
Figure 25C:
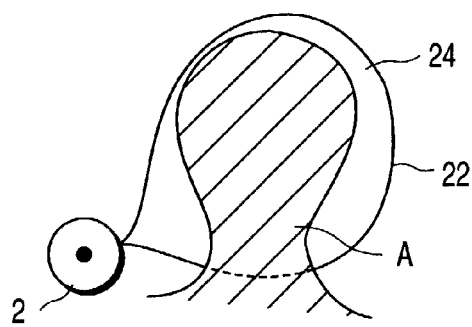
FIG. 25C is a view showing the second step as viewed from the direction 25C in FIG. 25B.
Figure 25E:
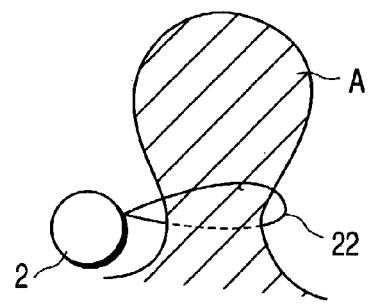
FIG. 25E is a view showing the third step as viewed from the direction 25E in FIG. 25D.

On the other hand, FIGS. 25A to 25E show a method of catching the loop portion 22 on the polyp A from its rear to tightly bind it. Specifically, first, as shown in FIG. 25A, the leading end of the sheath 2 is placed at the side of and behind the polyp A. In this state, the loop portion 22 is projected out of the side slit 2a. The loop portion 22 is also twisted to the degree that its opening surface 24 is not completely closed, so as to place the opening surface 24 behind and opposite the polyp A. This state is shown in FIGS. 25B and 25C. Then, in this state, the sheath 2 is retreated at the side of the polyp A. Then, the loop portion 22 can be caught on the polyp A as shown in FIGS. 25D and 25E.

It should be appreciated that the present invention is not limited to the previously described embodiments and many variations of them may be made without deviating from the spirit of the present invention. For example, in the previously described embodiments, a high-frequency current is used to excise biotissue. However, the biotissue excising instrument according to the present invention is not limited to electric excision. It is also applicable to various excision forms such as thermal and mechanical excisions.

What is claimed is:

1. A biotissue excision instrument comprising:
an elongated sheath having an outer peripheral wall defining an inner cavity therein, and a slit formed in the outer peripheral wall,
a loop wire which is inserted in the inner cavity and extending in an elongated direction of the sheath, the loop wire having two elongated portions and a tip bent portion which connects the elongated portions to each other, the elongated portions having separated distal end portions;
an engaging member which detachably engages the tip bent portion of the loop wire to the sheath; and
a manipulating member which is connected to the distal end of one of the elongated portions, and advances said one of the elongated portions to outwardly project a section of said one of the elongated portion in a loop shape through the slit when said tip bent portion of the loop wire is engaged with the engaging member, so that the loop shape section of the wire outwardly extended from the slit encloses a biotissue.

2. A biotissue excision instrument according to claim 1, wherein said distal ends of the elongated portions are positioned in the inner cavity when the tip bent portion of the loop wire is engaged with the sheath.

3. A biotissue excision instrument according to claim 2, further comprising a slider which is slidably inserted in the inner cavity and to which the distal end of the other elongated portion is fixed, said one elongated portion being movable against the slider.

4. A biotissue excising instrument comprising:
a loop member having a bent portion;
a manipulation member for operating the loop member so that the loop member excises a biotissue; and
a sheath having a distal end portion and a proximal end portion, the distal end portion having a cavity therein in which the loop member is received, the sheath having a slit formed in a side thereof, the slit being communicated with the cavity,
the cavity of the sheath having an engaging portion which is detachably engaged with the bent portion by elastic deformation of the bent portion,
the loop member being positioned in the cavity to be outwardly extendable through the slit in accordance with an operation of the manipulation member;
wherein said loop member has a closed loop portion formed by at least one wire, the closed loop portion is outwardly extendable from the slit.

5. A biotissue excising instrument according to claim 4, wherein said engaging portion is formed by reducing an inner diameter of the cavity, and the bent portion is inserted into the engaging portion and engaged thereto by a deformation of the bent portion.

6. A biotissue excising instrument according to claim 4, wherein a shoulder portion is formed at the leading end of the loop portion and abuts against a leading edge of the slit when the manipulation member is advanced toward the leading end of the sheath.

7. A biotissue excising instrument according to claim 6, wherein the inner diameter of area of the sheath which forms the slit is set to be equal to or larger than the length of area of the loop portion which projects toward the leading end beyond the shoulder portion.

8. A biotissue excising instrument according to claim 4, wherein the loop portion is formed of a solid wire.

9. A biotissue excising instrument according to claim 4, wherein the cavity of said sheath is formed to extend in an elongated direction of the sheath, the cavity having distal end side and a proximal end side, and said engaging portion is positioned on the distal end side of the cavity.

10. A biotissue excising instrument according to claim 9, wherein said bent portion has a guide for guiding the bent portion to the engaging portion.

11. A biotissue excising instrument according to claim 4, further comprising a slider provided so as to move freely toward to the proximal end portion of the sheath to advance and retreat the manipulation member,
wherein when the slider is located at a leading end of its moving path, the loop portion is unfolded maximally, and when the slider is located at a proximal end of its movement path, the loop portion sinks completely in an area of the sheath which is closer to the proximal end than the slit.

12. A biotissue excising instrument according to claim 4, further comprising a collar member arranged in the sheath to extend from a proximal edge of the slit toward the proximal end of the sheath by a predetermined length.

13. A biotissue excising instrument according to claim 12, wherein the collar member is formed to reinforce the sheath and prevent biotissue from entering the sheath.

14. A biotissue excising instrument according to claim 12, wherein the collar member has an extending portion extending from the proximal edge of the slit toward the leading end of the sheath by a predetermined length.

15. A biotissue excising instrument according to claim 4, further comprising an opening direction varying mechanism to vary the direction in which an opening surface of the loop portion is opened.

16. A biotissue excising instrument according to claim 15, wherein the opening direction varying mechanism is comprised of a tube fitted around an outer periphery of the sheath so as to advance and retreat freely, the tube having a leading end surface abutting against the loop portion projecting out of the slit to change the direction in which the loop portion projects.

17. A biotissue excising instrument according to claim 15, wherein the opening direction varying mechanism is comprised of a tube fitted around an outer periphery of the sheath so as to advance and retreat freely, the tube having at least one opening which is placed opposite the slit in the sheath from different directions depending on the amount by which the tube is moved relative to the sheath.

18. A biotissue excising instrument according to claim 1, further comprising a tube slidably fitted around an outer periphery of the sheath to close an opening of the slit.

19. A biotissue excising instrument according to claim 1, wherein the sheath has a holding portion which holds the loop portion substantially within one surface at the leading and proximal ends of the slit.

20. A biotissue excising instrument according to claim 15, wherein the loop portion is comprised of a first wire portion and a second wire portion which is harder than the first wire portion and which has a larger outer diameter than the first wire portion, and the loop portion is unfolded by projecting the first wire portion out of the slit, and wherein the first wire portion is provided with a tendency to bend in such a direction as resists twist of the loop portion.

21. A biotissue excision instrument according to claim 4, wherein said bent portion is deformable and elastically engaged with the engaging portion.

* * * * *